United States Patent
Oh et al.

(10) Patent No.: US 11,647,944 B2
(45) Date of Patent: May 16, 2023

(54) ELECTRONIC DEVICE FOR CONTROLLING SKIN-CARE DEVICE AND METHOD OF OPERATING THE SAME

(71) Applicant: SAMSUNG ELECTRONICS CO., LTD., Suwon-si (KR)

(72) Inventors: Youngjae Oh, Suwon-si (KR); Jinhong Min, Suwon-si (KR); Younjoo Song, Suwon-si (KR); Seoyoung Yoon, Suwon-si (KR); Sangkyung Lee, Suwon-si (KR); Joonho Kim, Suwon-si (KR); Changwon Son, Suwon-si (KR); Taehan Jeon, Suwon-si (KR); Hyoungseon Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 376 days.

(21) Appl. No.: 16/889,198

(22) Filed: Jun. 1, 2020

(65) Prior Publication Data

US 2020/0375526 A1    Dec. 3, 2020

Related U.S. Application Data

(60) Provisional application No. 62/855,216, filed on May 31, 2019.

(30) Foreign Application Priority Data

Sep. 26, 2019  (KR) .................. 10-2019-0119173

(51) Int. Cl.
*G06K 9/00* (2022.01)
*A61K 35/12* (2015.01)
(Continued)

(52) U.S. Cl.
CPC ............ *A61B 5/441* (2013.01); *A61B 5/0077* (2013.01); *A61B 5/0082* (2013.01);
(Continued)

(58) Field of Classification Search
CPC .......... G06K 9/00; G16K 30/40; A61K 35/12; A61B 5/441
(Continued)

(56) References Cited

U.S. PATENT DOCUMENTS 10,511,777 B2 * 12/2019 Nichols .............. H04N 5/23296
11,172,750 B2 * 11/2021 Park .................... B01F 33/8442
(Continued)

FOREIGN PATENT DOCUMENTS

CN        107427227 A      12/2017
JP        6445105 B2       12/2018
(Continued)

OTHER PUBLICATIONS

International Search Report (PCT/ISA/210) issued by the International Searching Authority in International Application No. PCT/KR2020/007084, dated Sep. 11, 2020.
(Continued)

*Primary Examiner* — Seyed H Azarian
(74) *Attorney, Agent, or Firm* — Sughrue Mion, PLLC

(57) ABSTRACT

According to an embodiment, an electronic device includes a camera, and at least one processor configured to: determine, from an image including a face of a user obtained via the camera, skin information indicating a skin condition of the user, generate control information for controlling a skin-care device to perform care based on the determined skin information and information regarding the skin-care device, and provide the control information to the skin-care device.

20 Claims, 26 Drawing Sheets

(51) Int. Cl.

| | |
|---|---|
| *A61B 5/00* | (2006.01) |
| *G16H 30/40* | (2018.01) |
| *A61B 5/1171* | (2016.01) |
| *G16H 10/60* | (2018.01) |
| *G16H 40/63* | (2018.01) |
| *G06T 7/00* | (2017.01) |
| *A61N 5/06* | (2006.01) |

(52) U.S. Cl.
CPC .......... *A61B 5/1176* (2013.01); *A61B 5/6803* (2013.01); *A61N 5/0616* (2013.01); *G06T 7/0012* (2013.01); *G16H 10/60* (2018.01); *G16H 30/40* (2018.01); *G16H 40/63* (2018.01); *A61B 2562/0257* (2013.01); *G06T 2207/30088* (2013.01); *G06T 2207/30201* (2013.01)

(58) Field of Classification Search
USPC ........ 382/100, 103, 106–108, 115, 123, 128, 382/154, 162, 168, 173, 181, 189, 192, 382/199, 203, 209, 219, 254, 276, 285, 382/291, 305, 312; 600/306, 490, 556, 600/557
See application file for complete search history.

(56) References Cited

U.S. PATENT DOCUMENTS

| | | | | |
|---|---|---|---|---|
| 2017/0061609 | A1* | 3/2017 | Son | ........................ G16H 30/40 |
| 2017/0340267 | A1 | 11/2017 | Shen et al. | |
| 2018/0014777 | A1 | 1/2018 | Amir et al. | |
| 2018/0106676 | A1* | 4/2018 | Jang | ...................... A61B 5/0075 |
| 2018/0137341 | A1 | 5/2018 | Jeong et al. | |
| 2019/0099614 | A1 | 4/2019 | Higgins et al. | |
| 2019/0336787 | A1* | 11/2019 | Kweon | ................. A45D 44/002 |
| 2021/0027897 | A1* | 1/2021 | Rasochova | .......... G06V 10/764 |

FOREIGN PATENT DOCUMENTS

| | | |
|---|---|---|
| KR | 10-1418972 B1 | 7/2014 |
| KR | 10-1492793 B1 | 2/2015 |
| KR | 10-2015-0137744 A | 12/2015 |
| KR | 10-2016-0110894 A | 9/2016 |
| KR | 10-2018-0054396 A | 5/2018 |
| KR | 10-2018-0085250 A | 7/2018 |
| KR | 10-2018-0097355 A | 8/2018 |
| KR | 10-2018-0134624 A | 12/2018 |
| KR | 10-1950504 B1 | 2/2019 |
| KR | 10-2019-0063041 A | 6/2019 |
| WO | 2018/236629 A1 | 12/2018 |

OTHER PUBLICATIONS

Written Opinion (PCT/ISA/237) issued by the International Searching Authority in International Application No. PCT/KR2020/007084, dated Sep. 11, 2020.
Communication dated Mar. 31, 2022 by the European Patent Office in counterpart European Patent Application No. 20813738.0.
Communication dated Jan. 12, 2023 issued by the China National Intellectual Property Administration in counterpart Chinese Patent Application No. 202080040408.5.

* cited by examiner

| TIME T1 | |
|---|---|
| SOLUTION | WEIGHT (TOTAL 1) |
| SOLUTION 1 | 0.5 |
| SOLUTION 2 | 0.2 |
| SOLUTION 3 | 0.3 |

UPDATE →

| TIME T2 | |
|---|---|
| SOLUTION | WEIGHT (TOTAL 1) |
| SOLUTION 1 | 0.6 |
| SOLUTION 2 | 0.15 |
| SOLUTION 3 | 0.25 |

ELECTRONIC DEVICE FOR CONTROLLING SKIN-CARE DEVICE AND METHOD OF OPERATING THE SAME

CROSS-REFERENCE TO RELATED APPLICATION(S)

This application is based on and claims priority under 35 U.S.C. § 119 to Korean Patent Application No. 10-2019-0119173, filed on Sep. 26, 2019, in the Korean Intellectual Property Office, and claims the benefit of U.S. Patent Application No. 62/855,216, filed on May 31, 2019, in the United States Patent and Trademark Office, and the disclosures of which are incorporated by reference herein in their entireties.

BACKGROUND

1. Field

The disclosure relates to an electronic device for controlling a skin-care device and a method for operating the same.

2. Description of Related Art

Recently, smart devices that measure a user's health information have become widely used. The user may measure his or her body-related information using an electronic device and manage his or her body and health conditions accordingly.

Also commonplace are skin-care devices that provide skin care for users in an easy and comfortable way. An example of such a skin-care device is a mask-type LED mask with multiple optical elements. The LED mask emits light from various light sources to the user's skin, prompting biochemical reactions in the skin, selectively regenerating or damaging skin tissues, and hence, treating damaged skin. Other types of skin-care devices include handheld-type cleansers, galvanic devices, and lifters.

Related art skin-care devices are operated in a preset operation mode. For example, related art skin-care devices may perform skin care and management according to one mode selected from preset operation modes. The skin-care devices may be driven based on the user's skin features entered by the user. None of the related art skin-care devices may analyze the user's current skin condition or face features and operate in a manner customized to the analyzed skin and face conditions. Thus, related art skin-care devices cannot deliver skin care that fits the user's skin condition and face shape.

SUMMARY

Provided are an electronic device capable of controlling a skin-care device to be suited for the user's skin condition and face shape and a method of operating the electronic device.

Additional aspects will be set forth in part in the description which follows and, in part, will be apparent from the description, or may be learned by practice of the presented embodiments.

In accordance with an aspect of the disclosure, an electronic device includes: a camera; and at least one processor configured to: determine, from an image including a face of a user obtained via the camera, skin information indicating a skin condition of the user, generate control information for controlling a skin-care device to perform care based on the determined skin information and information regarding the skin-care device, and provide the control information to the skin-care device.

In accordance with another aspect of the disclosure, a method for operating an electronic device includes: determining, from an image including a face of a user obtained via a camera of the electronic device, skin information indicating a skin condition of the user; generating control information for controlling a skin-care device to perform care based on the determined skin information and information regarding the skin-care device; and providing the control information to the skin-care device.

In accordance with another aspect of the disclosure, an electronic device includes: a communicator; and at least one processor configured to: determine whether a user is registered in the electronic device by comparing authentication information received from the user or a user terminal with pre-registered user information, based on the user being determined to be registered, send a request for control information for performing skin care appropriate for the user to an external electronic device via the communicator, and drive the electronic device based on the control information obtained from the external electronic device via the communicator, wherein the control information is generated by the external electronic device based on information indicating a shape and a function of the electronic device and skin information indicating a skin condition of the user determined from an image including a face of the user.

In accordance with another aspect of the disclosure, an electronic device includes: a communicator; and at least one processor configured to: determine skin information indicating a skin condition of a user from an image including a face of the user obtained via the communicator from an external electronic device, and provide control information for controlling a skin-care device to perform care corresponding to skin of the user based on the skin information and information regarding the skin-care device.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
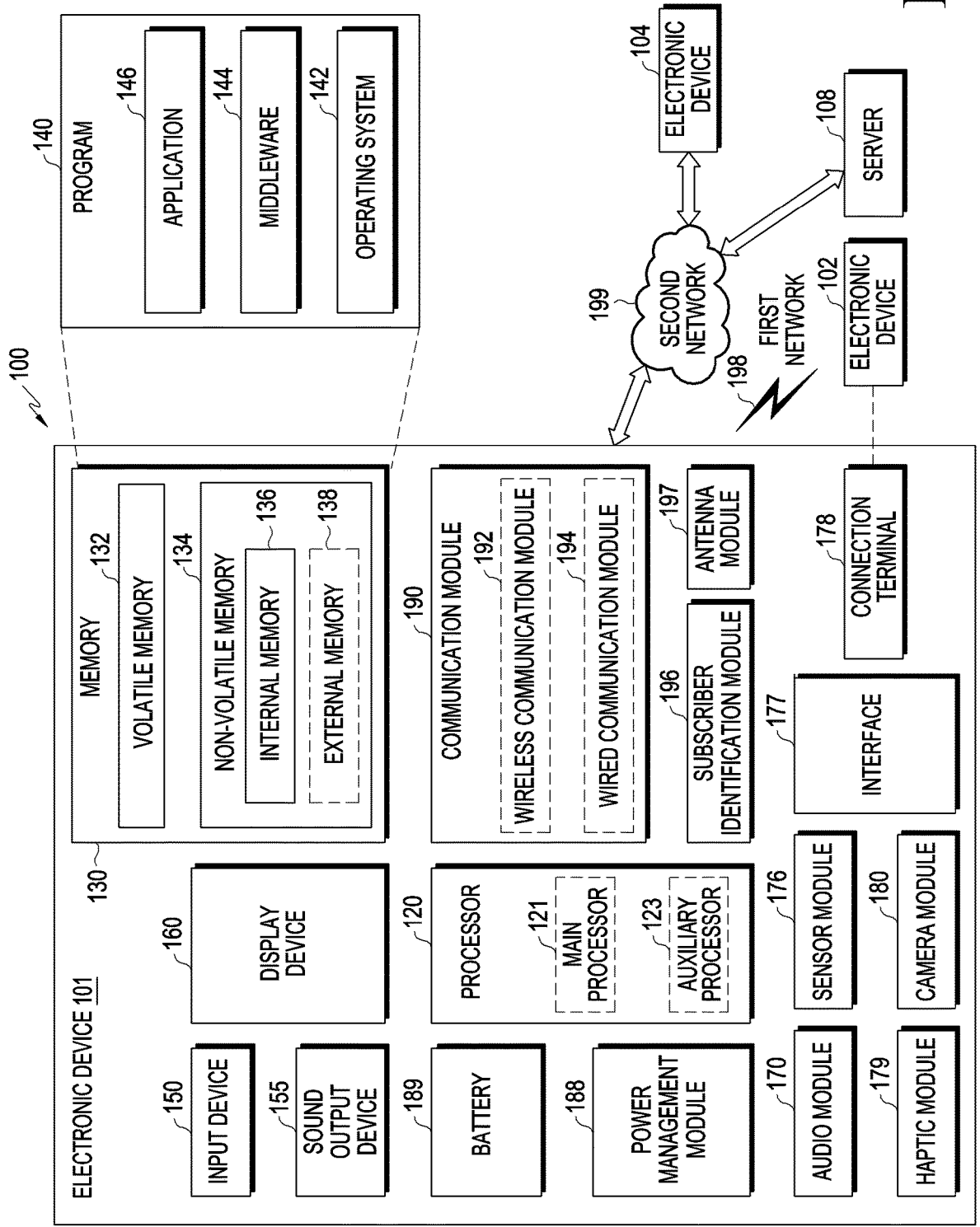
FIG. 1 is a view illustrating an electronic device in a network environment according to an embodiment.

FIG. 1 is a block diagram illustrating an electronic device 101 in a network environment 100 according to an embodiment. Referring to FIG. 1, the electronic device 101 (e.g., first electronic device) in the network environment 100 may communicate with an electronic device 102 (e.g., second electronic device) via a first network 198 (e.g., a short-range wireless communication network), or an electronic device 104 (e.g., third electronic device) or a server 108 (e.g., a cloud server) via a second network 199 (e.g., a long-range wireless communication network). According to an embodiment, the electronic device 101 may communicate with the electronic device 104 via the server 108. The electronic device 101 may include a processor 120 (e.g., at least one processor), memory 130, an input device 150, a sound output device 155, a display device 160, an audio module 170 (e.g., audio device or circuitry), a sensor module 176 (e.g., sensor, sensor circuitry), an interface 177, a haptic module 179 (e.g., haptic device or circuitry), a camera module 180 (e.g., camera), a power management module 188 (e.g., power manager, power management device, etc.), a battery 189, a communication module 190 (e.g., communication circuitry, communication interface, etc.), a subscriber identification module (SIM) 196, and an antenna module 197 (e.g., antenna, antenna device, antenna circuitry, etc.). In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware and/or software component) of the electronic device 101 coupled with the processor 120, and may perform various data processing or computation. As at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. The processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of, the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). The auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120, the sensor module 176, etc.) of the electronic device 101. The various data may include, for example, software (e.g., the program 140, instructions, code, etc.) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by another component (e.g., the processor 120) of the electronic device 101, from the outside (e.g., a user) of the electronic device 101. The input device 150 may include, for example, a microphone, a mouse, a keyboard, etc.

The sound output device 155 may output sound signals to the outside of the electronic device 101. The sound output device 155 may include, for example, a speaker or a receiver. The speaker may be used for general purposes, such as playing multimedia, and the receiver may be used for an incoming call. The receiver may be implemented as separate from, or as part of the speaker.

The display device 160 may visually provide information to the outside (e.g., a user) of the electronic device 101. The display device 160 may include, for example, a display, a hologram device, a projector, etc., and control circuitry to control a corresponding one of the display, hologram device, projector, etc. The display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. The audio module 170 may obtain the sound via the input device 150, or output the sound via the sound output device 155 or a headphone of an external electronic device (e.g., an electronic device 102) directly (e.g., via wire) or wirelessly coupled with the electronic device 101.

The sensor module 176 may detect an operational state (e.g., power, temperature, etc.) of the electronic device 101 or an environmental state (e.g., a state of a user) external to the electronic device 101, and then generate an electrical signal or data value corresponding to the detected state. The sensor module 176 may include, for example, at least one of a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, an illuminance sensor, etc.

The interface 177 may support one or more specified protocols to be used for the electronic device 101 to be coupled with the external electronic device (e.g., the electronic device 102) directly (e.g., via wire) or wirelessly. The interface 177 may include, for example, at least one of a high definition multimedia interface (HDMI), a universal serial bus (USB) interface, a secure digital (SD) card interface, an audio interface, etc.

A connecting terminal 178 may include a connector via which the electronic device 101 may be physically connected with the external electronic device (e.g., the electronic device 102). According to an embodiment, the connecting terminal 178 may include, for example, at least one of an HDMI connector, a USB connector, an SD card connector, an audio connector (e.g., a headphone connector), etc.

The haptic module 179 may convert an electrical signal into a mechanical stimulus (e.g., a vibration or motion) or electrical stimulus that may be recognized by a user via his tactile sensation or kinesthetic sensation. The haptic module 179 may include, for example, at least one of a motor, a piezoelectric element, an electric stimulator, etc.

The camera module 180 may capture a still image or moving images. The camera module 180 may include at least one of one or more lenses, image sensors, image signal processors, flashes, etc.

The power management module 188 may manage power supplied to the electronic device 101. The power management module 388 may be implemented as at least part of, for example, a power management integrated circuit (PMIC).

The battery 189 may supply power to at least one component of the electronic device 101. The battery 189 may include, for example, at least one of a primary cell that is not rechargeable, a secondary cell that is rechargeable, a fuel cell, etc.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., an application processor (AP)) and supports a direct (e.g., wired) communication or a wireless communication. The communication module 190 may include a wireless communication module 192 (e.g., at least one of a cellular communication module, a short-range wireless communication module, a global navigation satellite system (GNSS) communication module, etc.) or a wired communication module 194 (e.g., at least one of a local area network (LAN) communication module, a power line communication (PLC) module, etc.). A corresponding one of these communication modules may communicate with the external electronic device via the first network 198 (e.g., a short-range communication network, such as BLUETOOTH™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device). The antenna module 197 may include one or more antennas, and, therefrom, at least one antenna appropriate for a communication scheme used in the communication network, such as the first network 198 or the second network 199, may be selected or used, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, instructions or data may be transmitted or received between the electronic device 101 and the external electronic device 104 via the server 108 coupled with the second network 199. Each of the electronic devices 102 and 104 may be a device of a same type as, or a different type, from the electronic device 101. All or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To this end, a cloud computing, distributed computing, or client-server computing technology may be used, for example.

The electronic device according to various embodiments may be one of various types of electronic devices. The electronic devices may include, for example, a portable communication device (e.g., a smart phone), a computer device, a portable multimedia device, a portable medical device, a camera, a wearable device, a home appliance, etc., but are not limited thereto.

It should be appreciated that various embodiments of the disclosure and the terms used herein are not intended to limit the technological features set forth herein to particular embodiments, but include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, expressions such as "at least one of A and B," "at least one of A or B," "at least one of A, B, and C," and "at least one of A, B, or C," may include all possible combinations of the items enumerated together in a corresponding one of the phrases. As used herein, such terms as "1st" and "2nd," or "first" and "second," may be used to simply distinguish a corresponding component from another, and does not otherwise limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., via wire), wirelessly, or via a third (or intervening) element.

As used herein, the term "module" may include a unit implemented in at least one of hardware, software, or firmware, and may interchangeably be used with other terms, for example, "logic," "logic block," "part," or "circuitry." A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute the at least one instruction, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., PLAY STORE™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Hereinafter, the user's skin is assumed to be the face skin by default. However, this is merely for ease of description, and the technical spirit of the disclosure is not limited thereto.

Figure 2A:
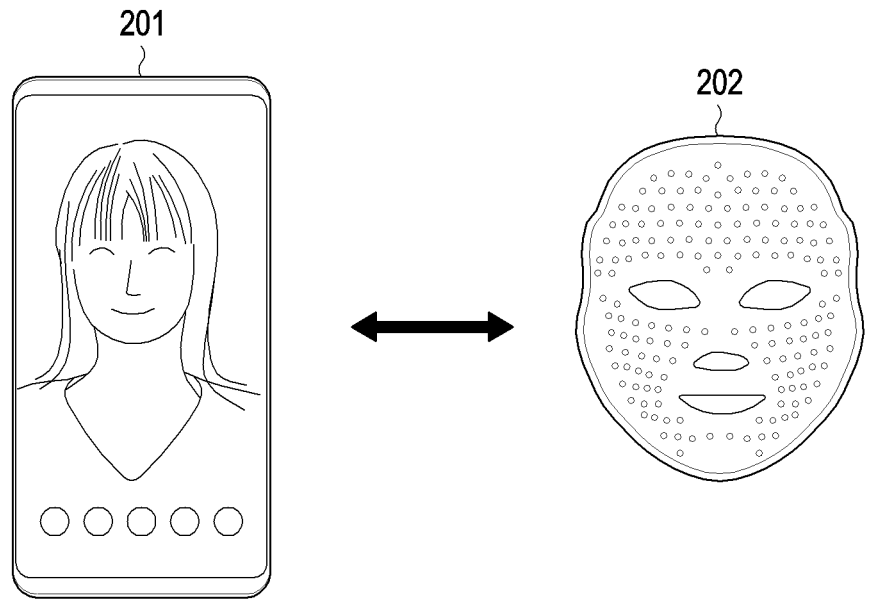
FIGS. 2A and 2B are block diagrams schematically illustrating an electronic system according to an embodiment.
Figure 2B:
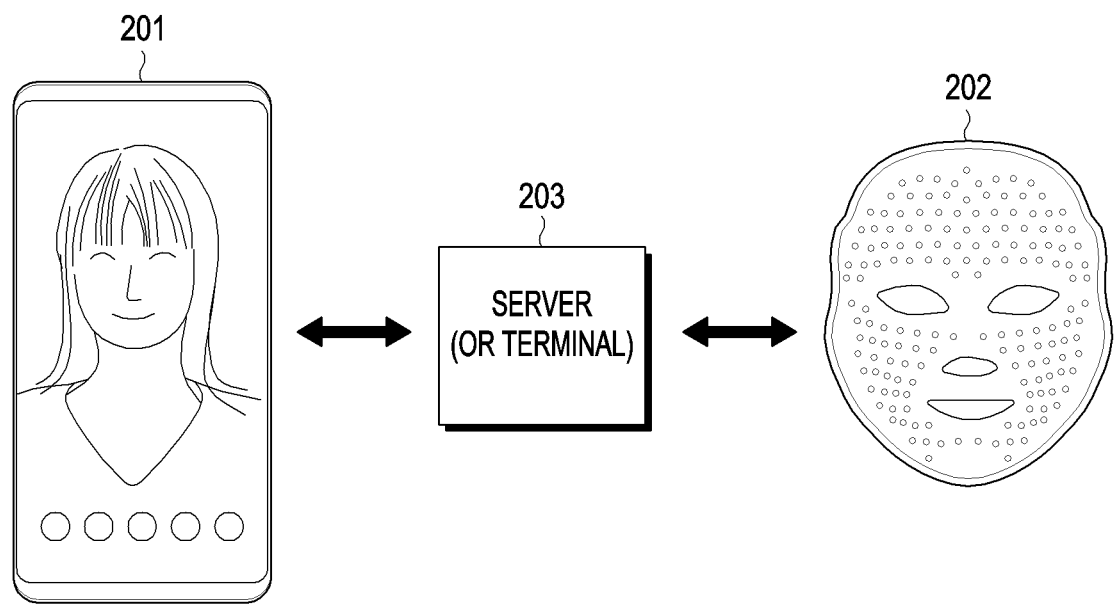

FIGS. 2A and 2B are block diagrams schematically illustrating an electronic system according to an embodiment.

Referring to FIG. 2A, an electronic system may include a first electronic device 201 and a second electronic device 202. For example, the electronic system may be implemented to be identical or similar to the network environment 100 of FIG. 1. The electronic system may include a system that is able to measure (or analyze) the user's skin and care for the skin.

According to an embodiment, the first electronic device 201 may measure the user's skin. For example, the first electronic device 201 may be implemented to be identical or similar to the electronic device 101 of FIG. 1. For example, the first electronic device 201 may include, e.g., a smartphone, tablet PC, smart mirror, etc., that is able to measure the user's skin via, e.g., a camera. For example, the smart mirror may refer to a device that combines a mirror and a display, and this device regularly functions as a mirror but, in a specific circumstance, e.g., when requested by the user, may perform a specific function via the display or display information related to the specific function.

According to an embodiment, the second electronic device 202 may include a skin-care device. For example, the second electronic device 202 may be implemented to be identical or similar to the electronic device 101, 102, or 104 of FIG. 1. For example, the skin-care device may refer to a device that may contact the user's skin directly or indirectly, e.g., by outputting at least one of a vibration, current, ions, a gas, or a specific frequency of light or high-frequency signal to the skin, to carry out a particular procedure on the user's skin. For example, the skin-care device may include a light emitting diode (LED) mask, skin massager (e.g., a galvanic massager and/or high-frequency massager), a lifter (or face lifter), a cleansing device, etc. Although FIG. 2A illustrates a mask-type device as the second electronic device 202, embodiments of the disclosure are not limited thereto. For example, according to another embodiment, the second electronic device 202 may also be implemented as a handheld-type device.

According to an embodiment, the first electronic device 201 may identify skin information that indicates the user's skin condition and/or skin feature. The first electronic device 201 may measure (or identify) face information that indicates at least one of the size or curves of the user's face, the sizes and positions of the features in the user's face, etc. For example, the first electronic device 201 may obtain an image including the user's face via the camera and identify the user's skin information (e.g., skin condition and features) and/or face information (e.g., the size and shape of the face) through the image.

Moreover, according to an embodiment, the first electronic device 201 may obtain information for the shape and function of the second electronic device 202. For example, the first electronic device 201 may identify the shape (e.g., coordinate information for the shape) of the second electronic device 202 from the second electronic device 202 and obtain information for what functions the second electronic device 202 may do.

Further, according to an embodiment, the first electronic device 201 may generate (or obtain) control information for controlling the second electronic device 202 based on the information indicating the shape and function of the second electronic device 202 and the user's skin information and face information. For example, the control information may include instructions or commands to allow, control, or instruction the second electronic device 202 to perform a specific operation so as to provide a skin-care method appropriate for the user (or the user's skin and face).

The first electronic device 201 may transmit the control information to the second electronic device 202 in response to (or based on) a request from the second electronic device 202 (e.g., a request to transmit the control information). For example, the first electronic device 201 may transmit the control information to the second electronic device 202 via a short-range communication technique (e.g., near-field communication (NFC), Bluetooth, Bluetooth low energy (BLE), wireless-fidelity (Wi-Fi), or peer-to-peer (P2P)) and/or wireless communication technology.

Referring to FIG. 2B, an electronic system may include a first electronic device 201, a second electronic device 202, and a server 203. For example, the electronic system may be implemented to be identical or similar to the network environment 100 of FIG. 1. The electronic system of FIG. 2B may further include the server 203 as compared with the electronic system of FIG. 2A. For example, the server 203 may include a computing device capable of performing the communication function, a cloud, a cloud server, a cloud computing device, or a server group (e.g., a front-end server or back-end server) of several types of servers.

According to an embodiment, the first electronic device 201 may communicate with the second electronic device 202 via the server 203. For example, the first electronic device 201 may transmit/receive control information to/from the second electronic device 202 via the server 203. The second electronic device 202 may communicate with the first electronic device 201 via the server 203. For example, the second electronic device 202 may receive control information from the first electronic device 201 via the server 203. The second electronic device 202 may transmit data (e.g., data related to the operation of the second electronic device 202) to the first electronic device 201 via the server 203.

Further, according to an embodiment, the server 203 may store the control information received from the first electronic device 201. For example, the server 203 may store the control information per user. The server 203 may store information about the user and store the control information in association with the user information. The server 203 may transmit control information to the second electronic device 202 in response to (or based on) a request from the second electronic device 202.

According to an embodiment, the server 203 may receive an image including the user's face (or face image) from the first electronic device 201 and generate or obtain control information based on the received image. For example, the server 203 may analyze the user's skin information (e.g., the skin condition and features of the user's face) included in the image and generate or obtain the control information based on the result of analysis. The server 203 may store the generated control information per user. The server 203 may store information about the user and store the control information in association with the user information. The server 203 may transmit control information to the second electronic device 202 in response to (or based on) a request from the second electronic device 202.

Additionally, the server 203 may adjust the control information based on additional information (e.g., information about the user's habit and/or ambient environment information). The server 203 may transmit the adjusted control information to the second electronic device 202 in response to (or based on) a request from the second electronic device 202.

Further, according to an embodiment, the server 203 may provide guide information including a method of using the second electronic device 202 (e.g., a skin-care device) based on the user's skin information and/or face information. For example, the guide information may refer to or include information indicating a method for the user to use the skin-care device 202, such as information about at least one of how to use the skin-care device, use time, effects of care, portions to be cared for, etc.

The server 203 may receive history information indicating the use history for the user from the second electronic device 202. For example, the history information may include the number of times in which the user has used the second electronic device 202 and/or the time of use by the user of the second electronic device 202 during a designated period. For example, the second electronic device 202 may periodically or aperiodically transmit the history information, which indicates the user's use history for the second electronic device 202, to the server 203.

According to an embodiment, the server 203 may obtain (or derive, determine, etc.) a solution for enhancing the user's skin (e.g., the user's skin condition) based on the user's skin information and/or face information. For example, the solution may refer to or include a method for enhancing the user's current skin. The solution may be determined considering the user's current skin condition and skin features. The solution may include a method of using the second electronic device 202 (e.g., the skin-care device). The server 203 may obtain and provide the solution further considering the history information. The server 203 may obtain and provide the control information for controlling the second electronic device 202 based on the solution. The solution may include the control information described herein. The solution may be control information for controlling or instructing the second electronic device 202.

For example, the server 203 may be implemented to be identical or similar to the server 108 of FIG. 1. Although FIG. 2B illustrates that the electronic system includes the server 203, embodiments of the disclosure are not limited thereto. For example, according to another embodiment, the server 203 may be replaced with a terminal (e.g., a smartphone, tablet PC, PC, or other computing device). The terminal may include at least one home device included in a home network.

Figure 3:
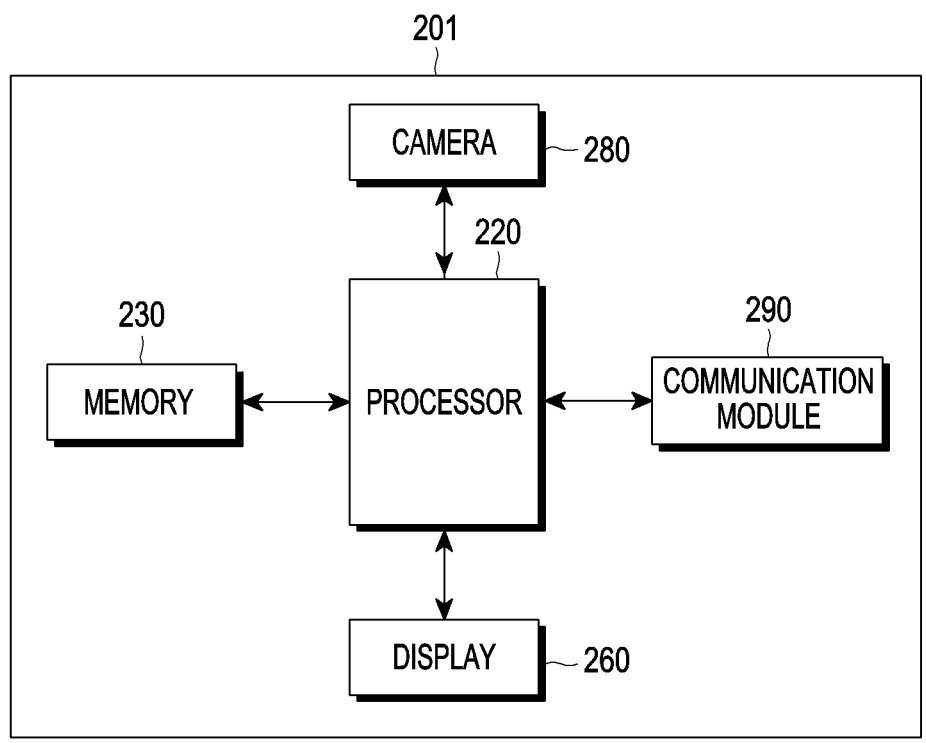
FIG. 3 is a block diagram schematically illustrating an electronic device according to an embodiment.

FIG. 3 is a block diagram schematically illustrating an electronic device 201 according to an embodiment.

Referring to FIG. 3, an electronic device 201 (e.g., first electronic device) may include a processor 220 (e.g., at least one processor), a memory 230, a display 260, a camera 280, and a communication module 290 (e.g., communication device, communication circuitry, communicator, communication interface, etc.).

The electronic device 201 may be implemented to be substantially identical or similar to the electronic device 201 of FIG. 2A or 2B. For example, the electronic device 201 may include a smartphone or a smart mirror.

The processor 220 may control the overall operation of the electronic device 201. For example, the processor 220 may be implemented to be identical or similar to the processor 120 of FIG. 1, and may include at least one processor.

According to an embodiment, the processor 220 may obtain an image including the user's face through the camera 280. The processor 220 may analyze the user's face included in the image and measure (or identify, determine, etc.) skin information indicating the user's skin condition and/or face information indicating the face shape according to the result of analysis. For example, the skin condition may include information about at least one of troubles, wrinkles, pores, skin texture, pigmentation, redness, porphyria, oily face, skin color, and other skin features (e.g., dry or oily skin). The face shape may include information about at least one of the size and curves of the face, the sizes and positions of the features in the face, etc.

According to an embodiment, the processor 220 may obtain information of the shape and function of the second electronic device 202. For example, the processor 220 may obtain information about the shape (e.g., coordinate information for the shape) of the second electronic device 202 and the functions that the second electronic device 202 may perform from the second electronic device 202. The processor 220 may obtain the information from the server 203.

The processor 220 may generate (or obtain, determine, etc.) control information based on the skin information indicating at least one of the user's skin condition, face information, and the information about the shape and function of the second electronic device 202. The processor 220 may store the control information in the memory 230. The processor 220 may transmit the control information to the second electronic device 202 via the communication module 290 in response to (or based on) a request from the second electronic device 202 (e.g., a request to transmit a control program).

Further, the processor 220 may display guide information related to the control information and/or a solution (or solution information) related to skin care. The processor 220 may provide results (or effects) expected when the user receives skin care via the control information to the display 260. For example, the processor 220 may display, on the display 260, details (e.g., at least one of what is cared for, driving time, or strength) of the control information and predicted results (e.g., the effect of enhancement by the care).

Figure 4:
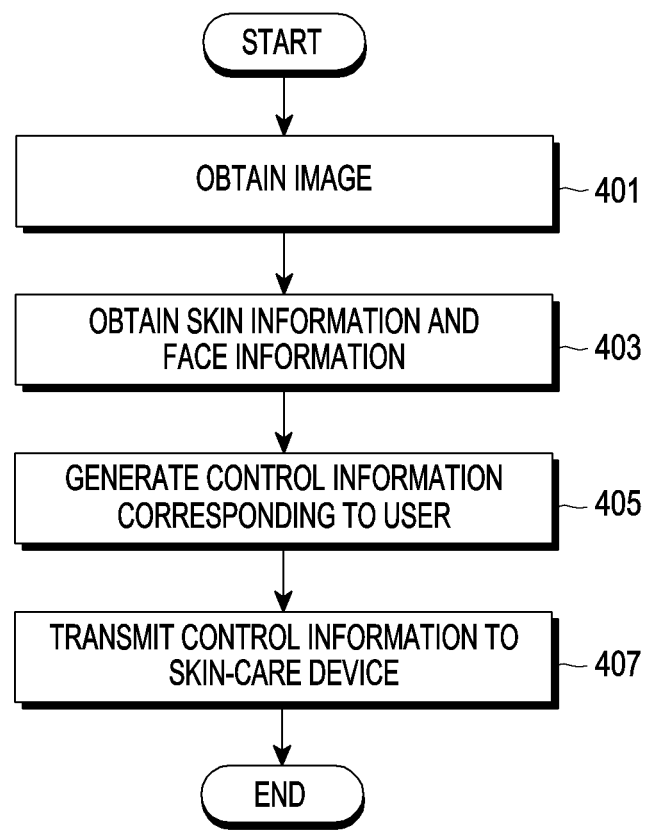
FIG. 4 is a flowchart illustrating a method of operating a skin measuring device according to an embodiment.

FIG. 4 is a flowchart illustrating a method of operating a skin measuring device according to an embodiment.

Referring to FIG. 4, in operation 401, a skin measuring device (e.g., the electronic device 201 of FIG. 3) may obtain an image including the user's face via a camera (e.g., the camera 280 of FIG. 3).

In operation 403, the skin measuring device 201 may obtain the user's skin information and face information from the user's face included in the image.

In operation 405, the skin measuring device 201 may generate (or obtain) control information corresponding to the user. For example, the skin measuring device 201 may generate control information for a skin-care device (e.g., the second electronic device 202 of FIG. 2) to perform skin care appropriate for the user based on the user's skin information and face information and information about the shape and function of the skin-care device. For example, the control information may include instructions for controlling the skin-care device to perform specific operations.

The skin measuring device 201 may store the control information corresponding to the user in a memory (e.g., the memory 230 of FIG. 3). The skin measuring device 201 may transmit the control information corresponding to the user to a server (e.g., the server 203 of FIG. 2B).

In operation 407, the skin measuring device 201 may transmit the control information to the skin-care device 202. For example, the skin measuring device 201, upon acknowledging a request from the skin-care device 202, may transmit the control information directly or via the server 203.

The server (e.g., the server 203 of FIG. 2B) may perform the above-described operations. The server 203 may obtain an image including the user's face from the skin measuring device 201. For example, the image may captured by the camera 280 of the skin measuring device 201. The server 203 may identify the user's skin information and face information from the user's face included in the image. The server 203 may generate (or obtain) the control information corresponding to the user. For example, the server 203 may generate control information for a skin-care device 202 to perform skin care appropriate for the user based on the user's skin information and face information and information about the shape and function of the skin-care device. The server 203 may store the control information corresponding to the user in a memory. For example, the server 203 may store the control information per user. The server 203 may transmit the control information corresponding to the user to the skin-care device 202.

Although described below is a method of generating control information by the skin measuring device 201 according to an embodiment, it is understood that the method may be performed by the server 203 according to another embodiment. In this case, the operation of generating control information by the server 203 may be identical or similar to the operation of generating control information by the skin measuring device 201.

Figure 5A:
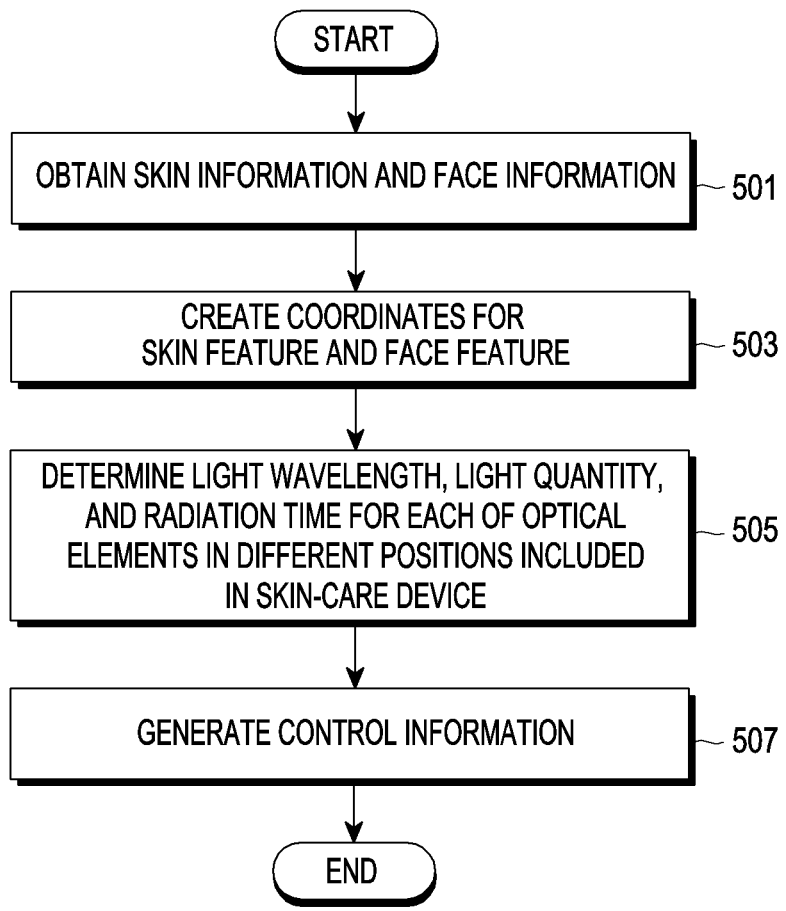
FIGS. 5A and 5B are flowcharts illustrating a method of generating a control program for controlling a skin-care device by a skin measuring device according to an embodiment.
Figure 5B:
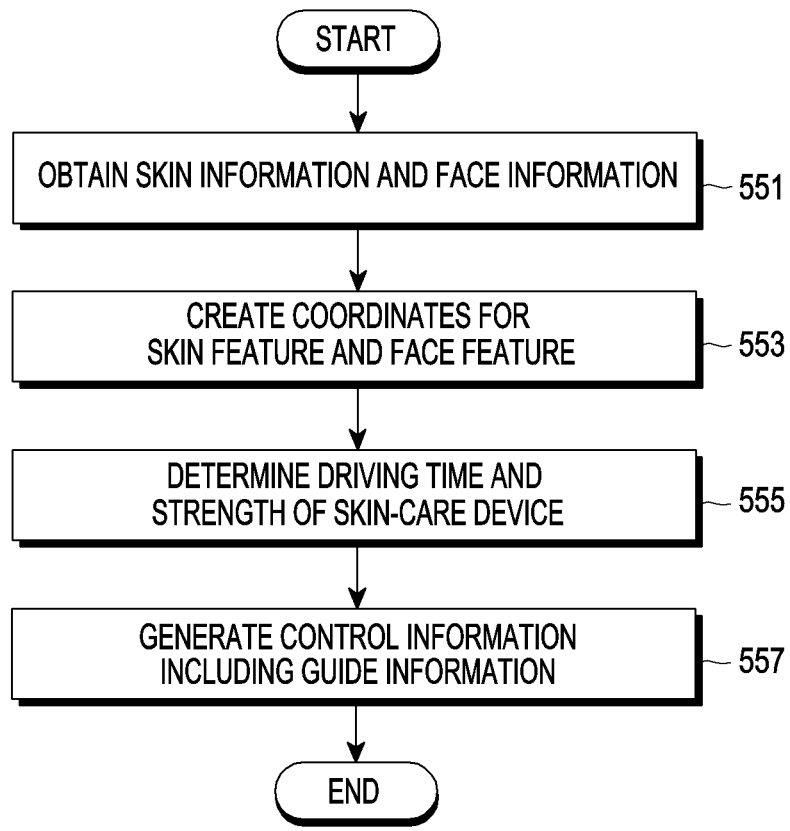

FIGS. 5A and 5B are flowcharts illustrating a method of generating a control program for controlling a skin-care device by a skin measuring device according to an embodiment.

FIG. 5A is a flowchart illustrating a method of operation of a skin measuring device (e.g., the first electronic device 201 of FIG. 2) when a skin-care device (e.g., the second electronic device 202 of FIG. 2) is an LED mask, according to an embodiment.

Referring to FIG. 5A, in operation 501, the skin measuring device (e.g., the first electronic device 201 of FIG. 3) may identify (or obtain, determine, etc.) the user's skin information and face information from an image including the user's face.

In operation 503, the skin measuring device 201 may create (or determine) coordinates for the positions of skin features and face features. For example, the skin measuring device 201 may obtain two-dimensional (2D) and/or three-dimensional (3D) coordinate information for the user's face. Further, by way of example, the skin measuring device 201 may identify at least one of the sizes and positions of the user's face features, the size and contour of the user's face, the number and positions of skin troubles (e.g., inflammation, acne, wrinkles, skin pores, pigmentation, redness, etc.) in the user's face, skin features (e.g., skin color, dry or oily skin), skin texture, porphyria, sebum, etc.

The skin measuring device 201 may obtain information about the shape and function of the skin-care device from the skin-care device 202 or server (e.g., the server 203 of FIG. 2B). For example, the skin measuring device 201 may identify that the skin-care device 202 functions as an LED mask. The skin measuring device 201 may identify that the skin-care device 202 is in the shape of a mask. The skin measuring device 201 may obtain position information about the positions of a plurality of optical elements included in the skin-care device 202.

The skin measuring device 201 may match the coordinate information for the user's face to the positions of the plurality of optical elements included in the skin-care device 202. For example, the skin measuring device 201 may identify at least one optical element that matches a specific portion of the user's face when (or based on) the user wears the skin-care device 202.

In operation 505, the skin measuring device 201 may determine at least one of the wavelength, amount, strength, or radiation time of light output from each of the plurality of optical elements in different positions included in the skin-care device 202. For example, the skin measuring device 201 may determine at least one of the wavelength, amount, strength, or radiation time of light output from at least one optical element that matches a specific portion of the user's face when the user wears the skin-care device 202. Here, the skin measuring device 201 may determine at least one of the wavelength, amount, strength, or radiation time of light considering the skin features of the specific face portion that matches the at least one optical element.

In operation 507, the skin measuring device 201 may generate (or obtain, determine, etc.) control information. For example, the control information may include setting values for the wavelength, amount, strength, and/or radiation time of light output from each of the plurality of optical elements. In other words, the control information may include information as to what setting values of light the skin-care device 202 outputs via each of the plurality of optical elements.

FIG. 5B is a flowchart illustrating a method of operation of a skin measuring device (e.g., the first electronic device 201 of FIG. 2) when a skin-care device (e.g., the second electronic device 202 of FIG. 2) is a handheld device, according to an embodiment.

Referring to FIG. 5B, in operation 551, the skin measuring device 201 may identify (or obtain, determine, etc.) the user's skin information and face information from an image including the user's face.

In operation 553, the skin measuring device 201 may create (or obtain, determine, etc.) coordinates for the positions of skin features and face features. For example, the skin measuring device 201 may obtain two-dimensional (2D) and/or three-dimensional (3D) coordinate information for the user's face. Further, the skin measuring device 201 may identify at least one of the sizes and positions of the user's face features, the size and contour of the user's face, the number and positions of skin troubles (e.g., inflammation, acne, wrinkles, skin pores, pigmentation, redness, etc.) in the user's face, skin features (e.g., skin color, dry or oily skin), skin texture, porphyria, and sebum.

The skin measuring device 201 may obtain information about the shape and function of the skin-care device from the skin-care device (e.g., the second electronic device 202 of FIG. 2) or server (e.g., the server 203 of FIG. 2B). For example, the skin measuring device 201 may identify that the skin-care device 202 is a handheld device. The skin measuring device 201 may be aware that the skin-care device 202 is a device (e.g., a high-frequency massager) capable of generating vibration and high-frequency signals.

In operation 555, the skin measuring device 201 may determine at least one of the output strength and driving time of vibration and high-frequency signal from the skin-care device 202. For example, the skin measuring device 201 may determine the output strength and driving time of vibration and high-frequency signal applied to a specific skin portion when the user touches the skin-care device 202 to the specific skin portion. At this time, the skin measuring device 201 may determine the output strength and driving time considering the skin features of the specific portion of the face.

In operation 557, the skin measuring device 201 may generate (or obtain, determine, etc.) control information. For example, the control information may include setting values for the output strength and driving time of vibration and high-frequency signal. In other words, the control information may include information about what setting values of vibration and high-frequency signals the skin-care device 202 outputs.

FIGS. 6A to 6D are views illustrating a method of providing a control program for controlling a skin-care device by a skin measuring device according to an embodiment.

Figure 6A:
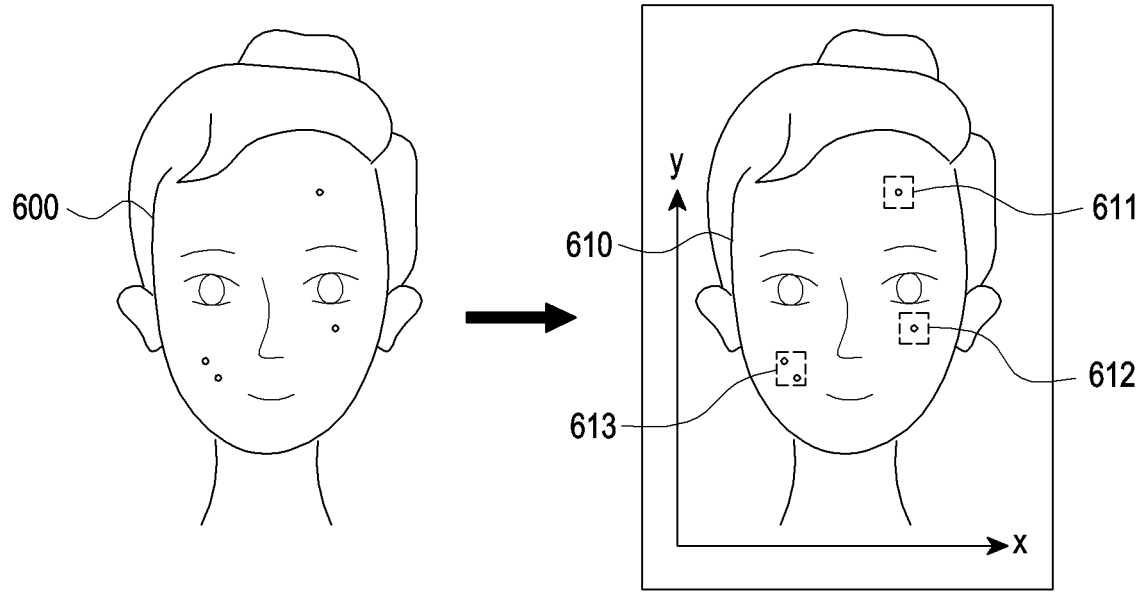
FIGS. 6A to 6D are views illustrating a method of providing a control program for controlling a skin-care device by a skin measuring device according to an embodiment.

Referring to FIG. 6A, a skin measuring device (e.g., the electronic device 201 of FIG. 3) may obtain an image 600 including a user's face via a camera (e.g., the camera 280 of FIG. 3).

According to an embodiment, the skin measuring device 201 may convert the image 600 into a 2D image 610. For example, the skin measuring device 201 may identify the size of the face and relative positions of at least one of the eyes, nose, mouth, and ears and obtain approximate x-y coordinate information for the eyes, nose, mouth, and ears. The skin measuring device 201 may also identify the positions of skin troubles that require (or may be suitable or determined for) skin care on the user's face. At this time, the skin measuring device 201 may identify the kind of corresponding skin troubles (e.g., wrinkles, acne, pimples, inflammations, pigmentation, skin pores, redness, and scars). For example, the skin measuring device 201 may obtain the x-y coordinate information about a first trouble 611, a second trouble 612, and a third trouble 613.

Figure 6B:
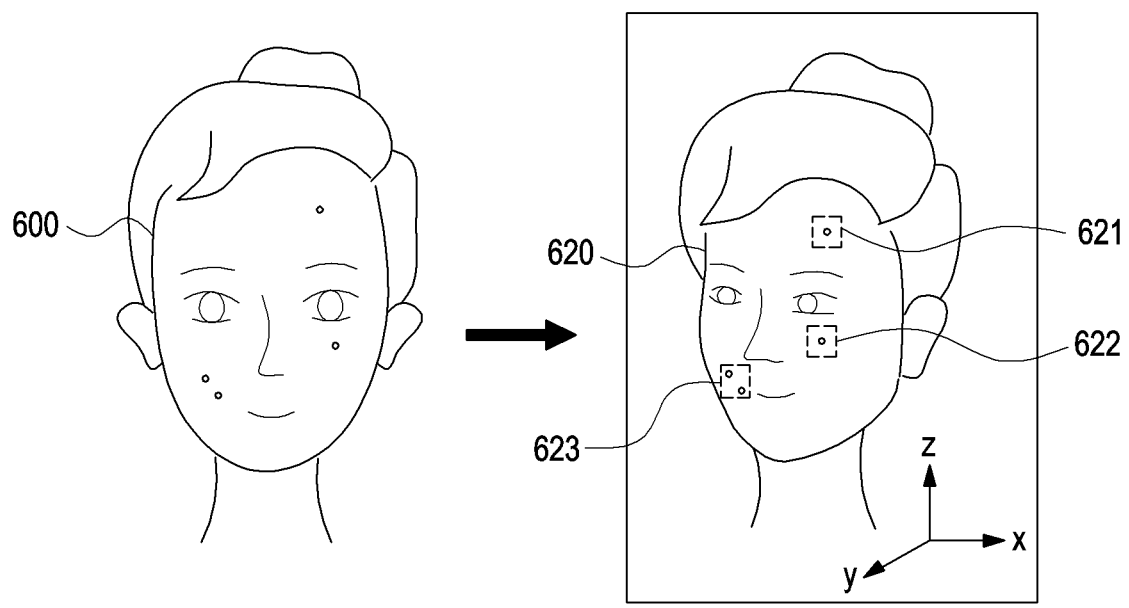

Referring to FIG. 6B, according to an embodiment, the skin measuring device 201 may convert the image 600 into a 3D image 620. For example, the skin measuring device 201 may identify the size of the face and relative positions of the eyes, nose, mouth, and ears and obtain approximate x-y-z coordinate information for the eyes, nose, mouth, and ears. The skin measuring device 201 may also identify the positions of skin troubles that require (or may be suitable or determined for) skin care on the user's face. Further, the skin measuring device 201 may identify the kind of corresponding skin troubles (e.g., wrinkles, acne, pimples, inflammations, pigmentation, skin pores, redness, and scars). For example, the skin measuring device 201 may obtain the x-y-z coordinate information about a first trouble 621, a second trouble 622, and a third trouble 623.

Figure 6C:
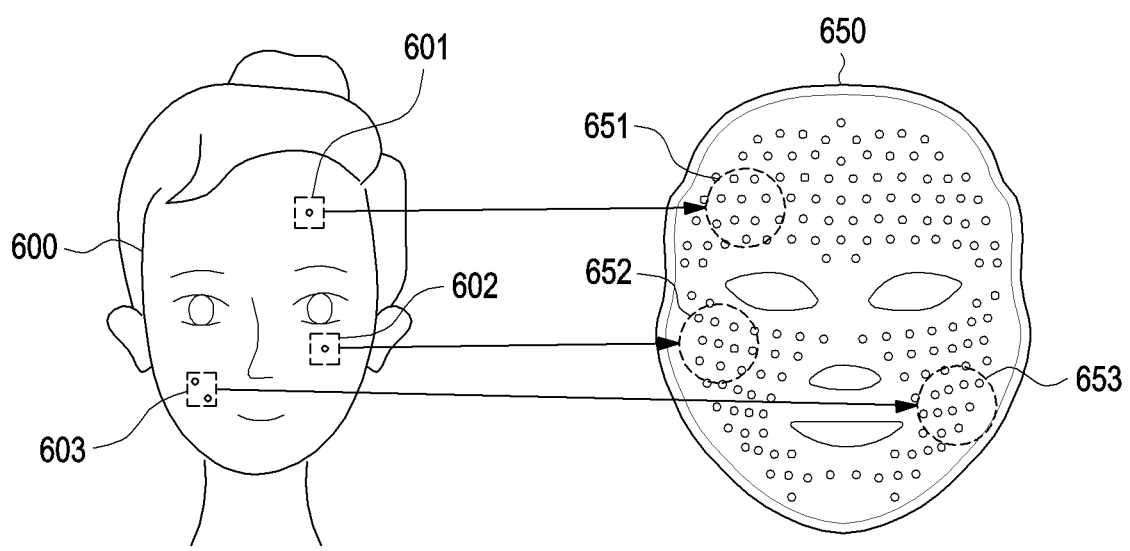

Referring to FIG. 6C, the skin measuring device 650 (For example, the skin measuring device 201) may match the positions of the plurality of skin troubles 601, 602, and 603 included in the image 600 to the areas of the plurality of optical elements included in the skin measuring device 650 using at least one of the 2D image 620 and the 3D image 630. For example, the skin measuring device 201 may match the first trouble 601 to a first area 651, the second trouble 602 to a second area 652, and the third trouble 603 to a third area 653.

According to an embodiment, the skin measuring device 201 may identify the kind of the plurality of troubles 601, 602, and 603 and determine a caring method appropriate for the kind of trouble. For example, if the first trouble 601 is wrinkles, the skin measuring device 201 may determine to radiate a specific wavelength of light (e.g., yellow light) appropriate for reducing wrinkles to the first area 651. If the second trouble 602 is a scar, the skin measuring device 201 may determine to radiate a weak strength of light to the second area 652. If the third trouble 603 is a pimple, the skin measuring device 201 may determine to radiate a specific wavelength of light (e.g., blue light) appropriate for mitigating pimples to the third area 653. The skin measuring device 201 may generate (or obtain) control information based on the caring method appropriate for the determined kind of trouble. The skin-care device 650 may be driven, with the determined caring method applied to the first area 651, second area 652, and third area 653, based on the control information. The skin-care device 650 may radiate red light and/or infrared (IR) light, as a default, to the other areas based on the control information. The skin-care device 650 may refrain from radiating light to at least some of the other areas based on the control information.

According to an embodiment, the skin measuring device 201 may more precisely identify the position of the skin trouble using the 3D image 620 as compared to using the 2D image 610. The skin measuring device 201 may combine the 2D image 610 with the 3D image 620, thereby identifying the position of the skin trouble in an even more precise manner.

Figure 6D:
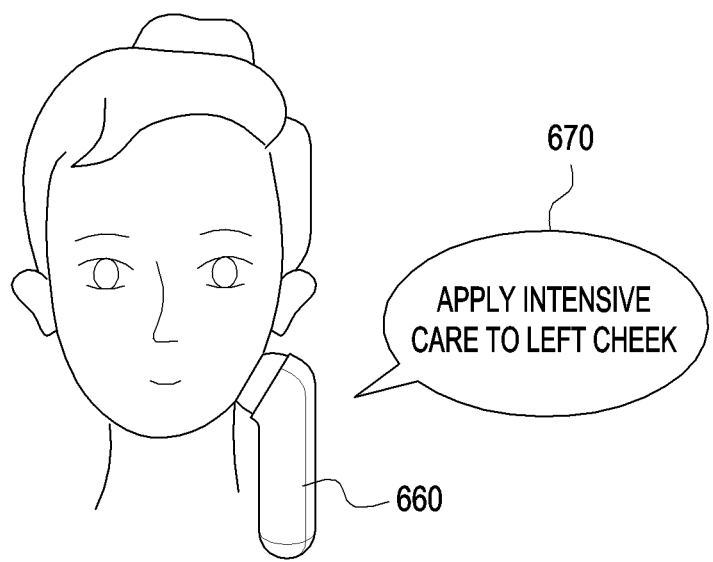

Referring to FIG. 6D, the skin measuring device 201 may determine a caring method appropriate for the kind of skin-care device 660.

According to an embodiment, the skin measuring device 201 may identify the position and kind of skin trouble in the image 600 and determine a caring method appropriate for the corresponding skin trouble based on the kind of the skin-care device 660. For example, if the skin-care device 660 is a handheld device, the skin measuring device 201 may identify the approximate position of the skin trouble. The skin measuring device 201 may determine a solution 670 for the position of the skin trouble and the caring method. For example, the skin measuring device 201 may determine that the position of the skin trouble is the "left cheek," and determine the solution 670 to "apply intensive care to your left cheek area." The skin measuring device 201 may generate (or obtain, determine, etc.) control information based on the determined solution 670. The skin-care device 660 may be driven based on the control information, while providing the determined solution, e.g., in a voice.

Figure 7:
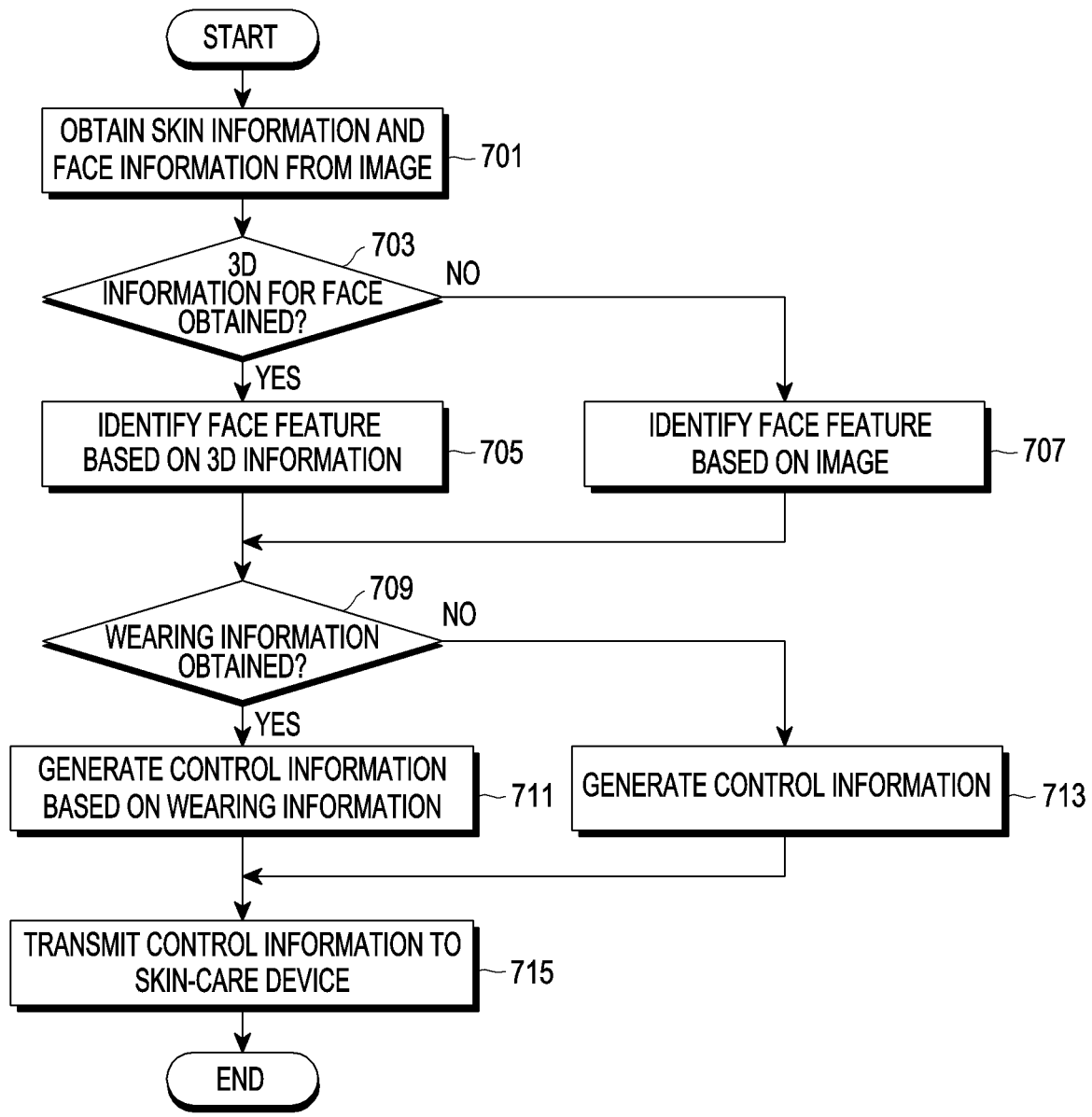
FIG. 7 is a flowchart illustrating a method of generating a control program for controlling a skin-care device by a skin measuring device according to an embodiment.

FIG. 7 is a flowchart illustrating a method of generating a control program for controlling a skin-care device by a skin measuring device according to an embodiment.

Referring to FIG. 7, in operation 701, a skin measuring device (e.g., the electronic device 201 of FIG. 3) may obtain the user's skin information and face information from an image including the user's face. For example, the image may be a 2D image.

In operation 703, the skin measuring device 201 may identify whether 3D image information for the user's face has been obtained.

In operation 705, the skin measuring device 201 may identify face features (e.g., skin information and face information) based on the 3D image information. In operation 707, absent the 3D image information (e.g., based on the 3D information not being obtained), the skin measuring device 201 may identify face features (e.g., skin information and face information) based on the 2D image information.

In operation 709, the skin measuring device 201 may identify whether wearing information has been obtained from a skin-care device (e.g., the second electronic device 202 of FIG. 2). For example, the wearing information may be or include information indicating how the user has worn the skin-care device 202. The wearing information may include information about how tight the skin-care device 202 comes in contact with the user. For example, the wearing information may include information indicating that a specific portion of the user's face more tightly contacts a specific area of the skin-care device 202 while another portion of the user's face less tightly contacts another area of the skin-care device 202. The wearing information may be measured or obtained by at least one proximity sensor included in the skin-care device 202. For example, the at least one proximity sensor may be placed in the position where the skin-care device 202 contacts the user's skin. In this case, the wearing information may include information indicating the degree of tightness between the user's face skin and the skin-care device 202 by at least one proximity sensor included in the skin-care device 202.

In operation 711, the skin measuring device 201 may generate control information based on the identified face features and wearing information. For example, the skin measuring device 201 may generate control information for more accurately performing or providing skin care considering the wearing information.

In operation 713, the skin measuring device 201 may generate control information based on the identified face features. That is, the skin measuring device 201 may generate control information considering the identified face features without considering the wearing information, e.g., based on the wearing information not being obtained.

In operation 715, the skin measuring device 201 may transmit the generated control information to the skin-care device 202. The skin measuring device 201 may transmit the control information to a server (e.g., the server 203 of FIG. 2B) so that the control information is transmitted to the skin-care device 202.

Figure 8A:
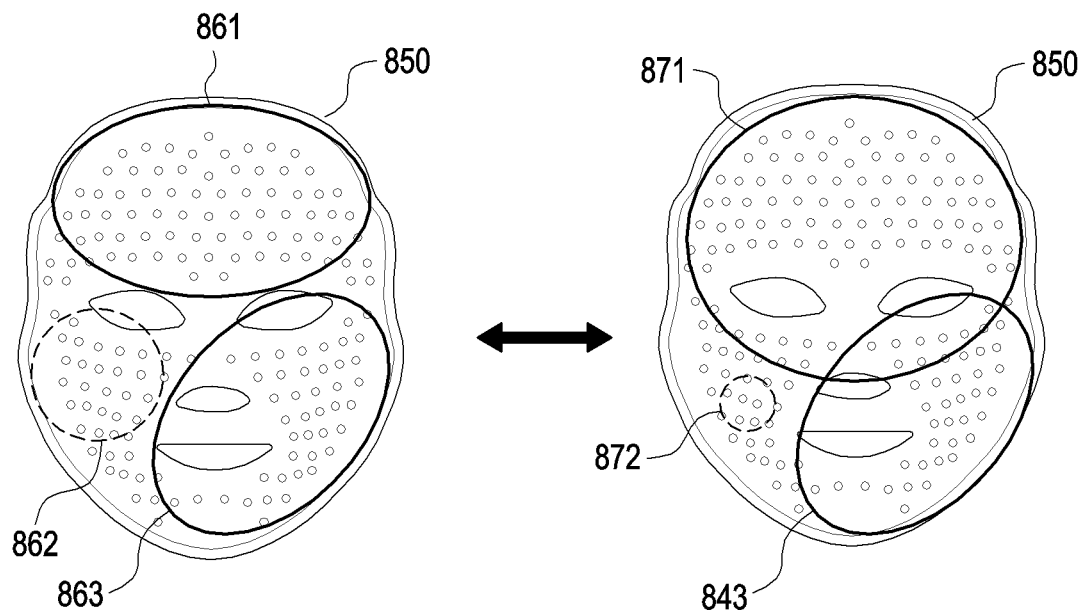
FIGS. 8A and 8B are views illustrating a method of providing a control program for controlling a skin-care device by a skin measuring device according to an embodiment.
Figure 8B:
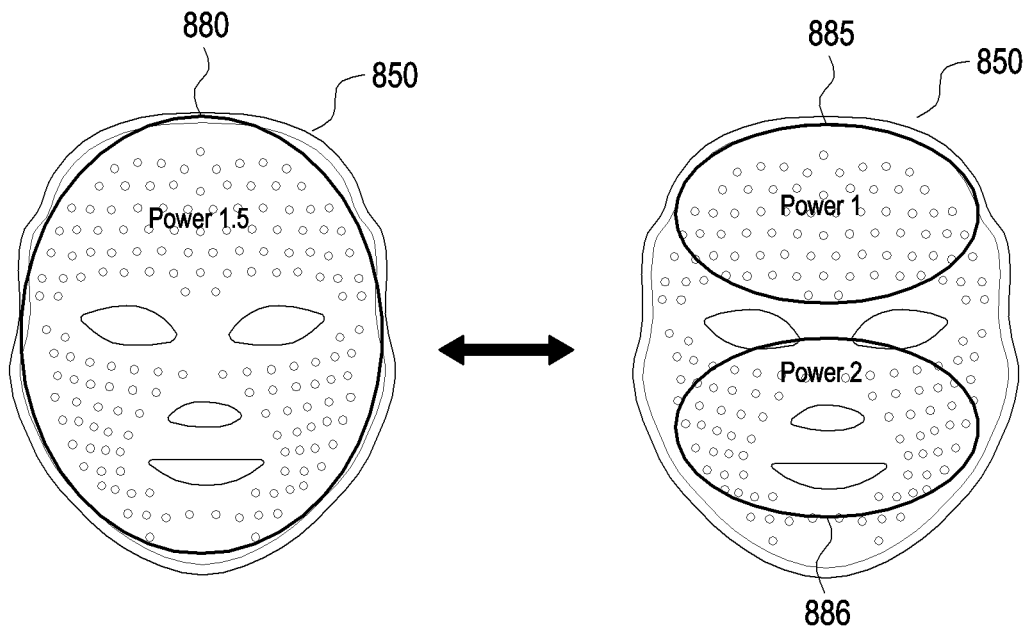

FIGS. 8A and 8B are views illustrating a method of providing a control program for controlling a skin-care device 850 by a skin measuring device according to an embodiment.

According to an embodiment, a skin measuring device 850 (e.g., the electronic device 201 of FIG. 3) may generate control information for more precisely performing skin care using wearing information and information about a 3D image (e.g., the image 620 of FIG. 6B).

Referring to FIGS. 8A and 8B, according to an embodiment, the skin-care device 850 may output red light to a first area 861 and a third area 863 and blue light to a second area

862. The skin-care device 850 may output a different strength of light to each of the first area 861 and the third area 863.

Referring to FIG. 8A, according to an embodiment, the skin-care device 850 may perform intensive skin care to the first area 861, second area 862, and third area 863 based on the control information generated without using the wearing information and the 3D image-related information. Alternatively, the skin-care device 850 may perform intensive skin care to the first area 871, second area 872, and third area 873 based on the control information generated using at least one of the wearing information and the 3D image-related information. In other words, the skin-care device 850 may provide skin care to the user's face (or face shape) using the control information generated based on the 3D image-related information and the wearing information. For example, the first area 871, second area 872, and third area 873 may be areas accurately targeted to the user's skin (e.g., skin trouble).

Referring to FIG. 8B, according to an embodiment, the skin-care device 850 may output a 1.5 strength of light to the fourth area 880 based on the control information generated without using the 3D image-related information and wearing information. Alternatively, the skin-care device 850 may perform skin care on the fifth area 885 in a first strength and output a second strength of light to the sixth area 886 using the control information generated based on at least one of the 3D image-related information and wearing information. In other words, the skin-care device 850 may provide accurate skin care (e.g., output light) to the user's face using the control information generated using at least one of the 3D image-related information and wearing information. For example, if the user's forehead relatively sticks out, the skin-care device 850 may output a relatively low strength of light to the fifth area 885, which corresponds to the forehead, and a relatively high strength of light to the sixth area 886.

Figure 9A:
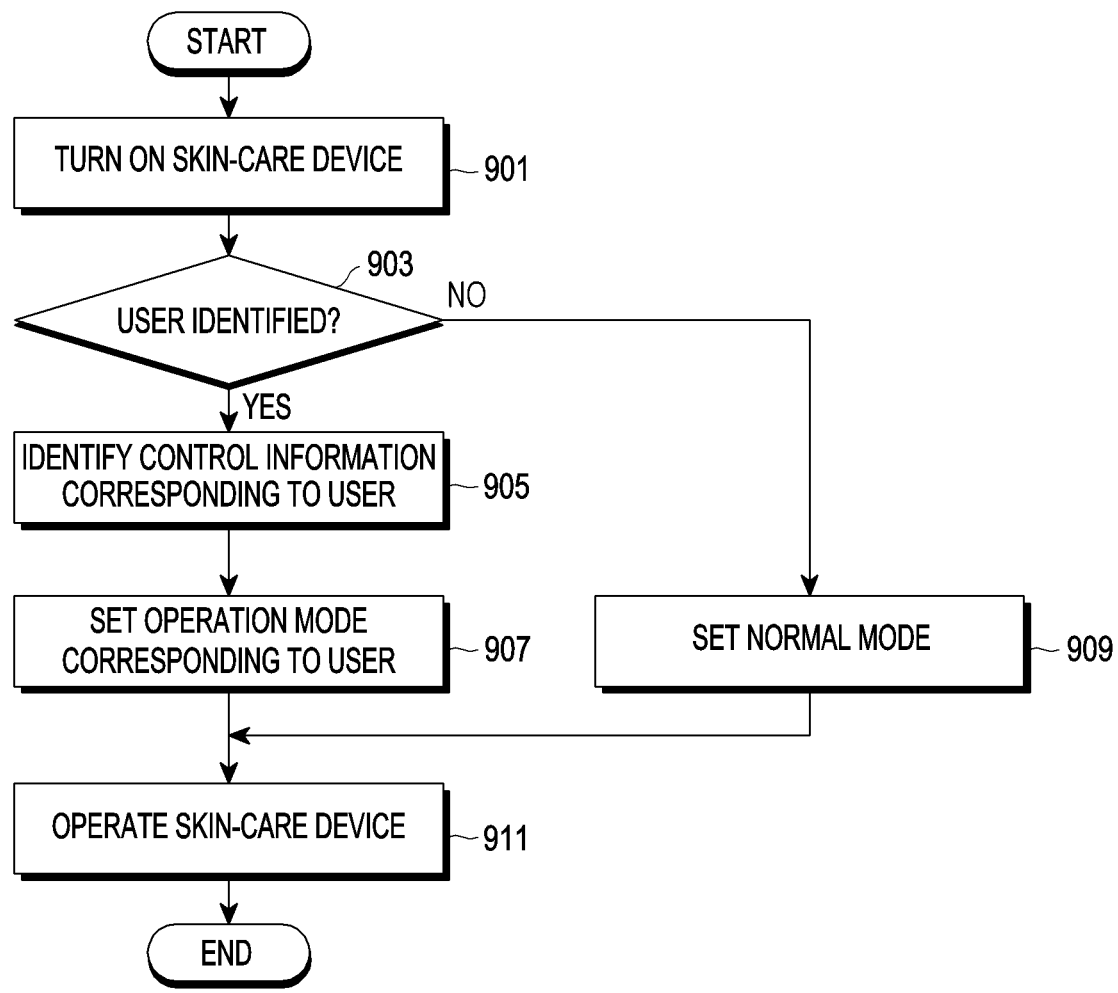
FIGS. 9A and 9B are flowcharts illustrating a method of operating a skin-care device according to an embodiment.
Figure 9B:
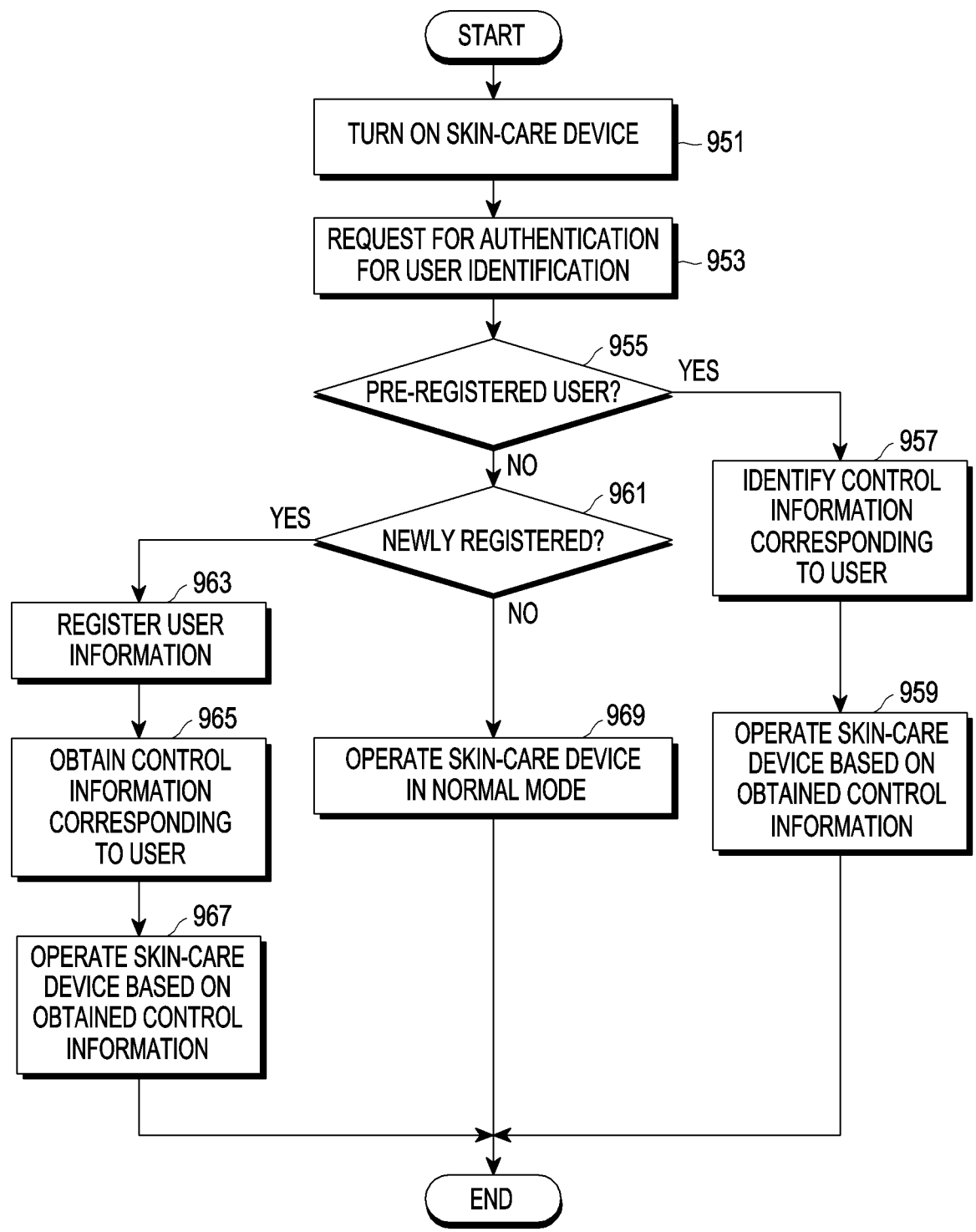

FIGS. 9A and 9B are flowcharts illustrating a method of operating a skin-care device according to an embodiment.

FIG. 9A is a flowchart illustrating operations of identifying the user and providing skin care by the skin-care device according to an embodiment.

Referring to FIG. 9A, in operation 901, the skin-care device (e.g., the second electronic device 202 of FIG. 2) may be turned on by the user.

In operation 903, the skin-care device 202 may identify the user. For example, the skin-care device 202 may receive at least one of predetermined user information (e.g., fingerprint, voice, pin number, iris, or face scanning) or ID information and identify whether the user is a registered one. The skin-care device 202 may receive a short-range communication signal (e.g., a near-field communication (NFC) signal) from the user's terminal (e.g., a smartphone) and identify whether the user is a registered user. For example, the skin-care device 202 may receive user information (e.g., ID information) from the user's terminal via short-range communication and identify whether the user is a pre-registered in the skin-care device 202 based on the user information.

In operation 905, the skin-care device 202, if (or based on) the user is identified, may identify control information corresponding to the identified user. For example, the skin-care device 202, if the user is identified, may send a request for control information for the user to a skin measuring device (e.g., the first electronic device 201 of FIG. 2) or a server (e.g., the server 203 of FIG. 2B). The skin-care device 202 may obtain control information for the user from the skin measuring device 201 or the server 203.

In operation 907, the skin-care device 202 may set the operation mode to a user mode corresponding to the user according to the control information. In operation 909, the skin-care device 202, unless the user is identified, may set the operation mode to a normal mode, without control information. For example, the normal mode may be or correspond to a mode in which the skin-care device 202 normally operates without specific settings.

In operation 911, the skin-care device 202 may operate according to the set mode. In other words, the skin-care device 202, if (or based on) the user is identified, may provide skin care appropriate for the user according to the control information. In contrast, the skin-care device 202, if (or based on) the user is not identified, may provide skin care in the normal mode, although one or more other embodiments are not limited thereto. For example, according to another embodiment, if the user is not identified, the skin-care device 202 may provide skin care according to a preset operation mode.

FIG. 9B is a flowchart illustrating an operation of registering user information for identifying the user by the skin-care device according to an embodiment.

Referring to FIG. 9B, in operation 951, the skin-care device (e.g., the second electronic device 202 of FIG. 2) may be turned on by the user.

In operation 953, the skin-care device 202 may request authentication information for identifying the user. For example, the skin-care device 202 may request the authentication information via a notification on a display included in the skin-care device 202 or via a voice. For example, the authentication information may include at least one of a voice, pin number, iris, face scan, ID information, etc.

In operation 955, the skin-care device 202 may identify whether the user is a previously-registered user. For example, the skin-care device 202 may compare the received authentication information with pre-stored authentication information, thereby identifying whether the user is a registered user.

In operation 957, the skin-care device 202, if (or based on) the user is identified, may identify control information corresponding to the identified user. For example, the control information may be obtained from a skin measuring device (e.g., the first electronic device 201 of FIG. 2) or a server (e.g., the server 203 of FIG. 2B).

In operation 959, the skin-care device 202 may be operated based on the identified control information.

In operation 961, the skin-care device 202 may identify whether the user newly registers user information if (or based on) the user not being identified as a pre-registered user. For example, the skin-care device 202 may inquire about the new registration via the display included in the skin-care device 202 and/or via a voice.

In operation 963, the skin-care device 202 may register the user information. For example, the user information may include authentication information about the user. The skin-care device 202 may send a request for control information to the skin measuring device (e.g., the first electronic device 201 of FIG. 2) or server (e.g., the server 203 of FIG. 2B), along with registration of the user information. The control information may be generated by the skin measuring device 201.

In operation 965, the skin-care device 202 may obtain a control program or control information corresponding to the user. For example, the skin-care device 202 may obtain control information from the skin measuring device 201 or the server 203. In operation 967, the skin-care device 202 may be operated based on the obtained control information.

In operation 969, if the user does not request new registration, skin care may be provided in the normal mode.

FIGS. 10A to 10F are flowcharts illustrating a method of operating an electronic system according to an embodiment.

Figure 10A:
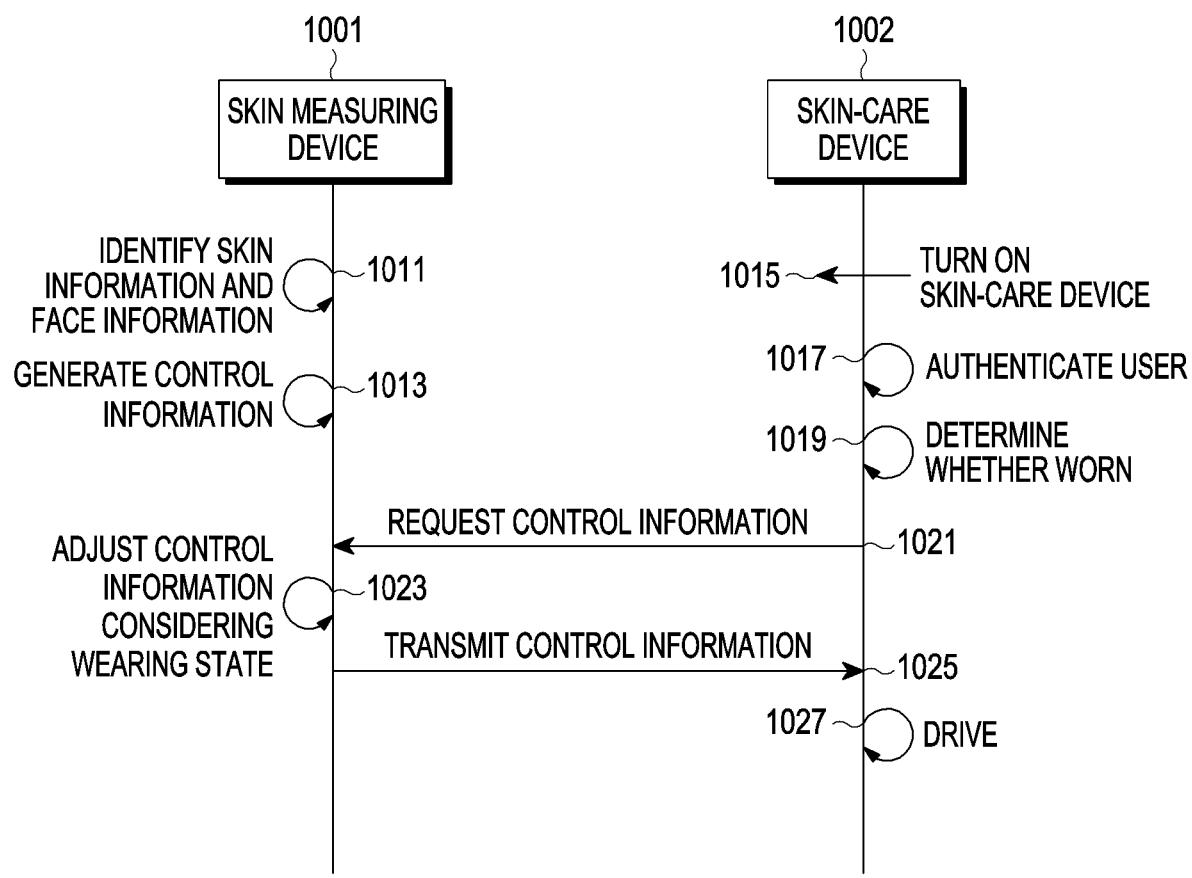
FIGS. 10A to 10F are flowcharts illustrating a method of operating an electronic system according to an embodiment.

FIG. 10A is a flowchart illustrating a method in which a skin-care device 1002 obtains control information generated by a skin measuring device 1001 and is driven based on the control information.

According to an embodiment, referring to FIG. 10A, the skin measuring device 1001 and the skin-care device 1002 are in a state of directly communicating with each other.

Referring to FIG. 10A, in operation 1011, the skin measuring device 1001 (e.g., the first electronic device 201 of FIG. 2A) may identify the user's skin information and face information from an image including the user's face.

In operation 1013, the skin measuring device 1001 may generate control information corresponding to the user (or the user's face).

In operation 1015, the skin-care device 1002 (e.g., the second electronic device 202 of FIG. 2A) may be turned on by the user. In operation 1017, the skin-care device 1002 may request user authentication. In operation 1019, if user authentication is successful, the skin-care device 1002 may determine whether the user has worn the skin-care device 1002.

In operation 1021, the skin-care device 1002 may send a request for control information to the skin measuring device 1001. For example, if (or based on) the user has worn the skin-care device 1002, the skin-care device 1002 may transmit wearing information to the skin measuring device 1001 while (e.g., prior to, concurrently with, or after) requesting the control information. In contrast, if the user has not worn the skin-care device 1002, the skin-care device 1002 may request control information without transmitting wearing information.

In operation 1023, the skin measuring device 1001 may adjust the control information considering or based on the wearing state. For example, upon (or based on) receiving the wearing information, the skin measuring device 1001 may adjust the control information based on the wearing information. Absent reception of the wearing information (or based on not receiving the wearing information), the skin measuring device 1001 may refrain from adjusting the control information.

In operation 1025, the skin measuring device 1001 may transmit the control information to the skin-care device 1002. In operation 1027, the skin-care device 1002 may be driven according to the control information.

Figure 10B:
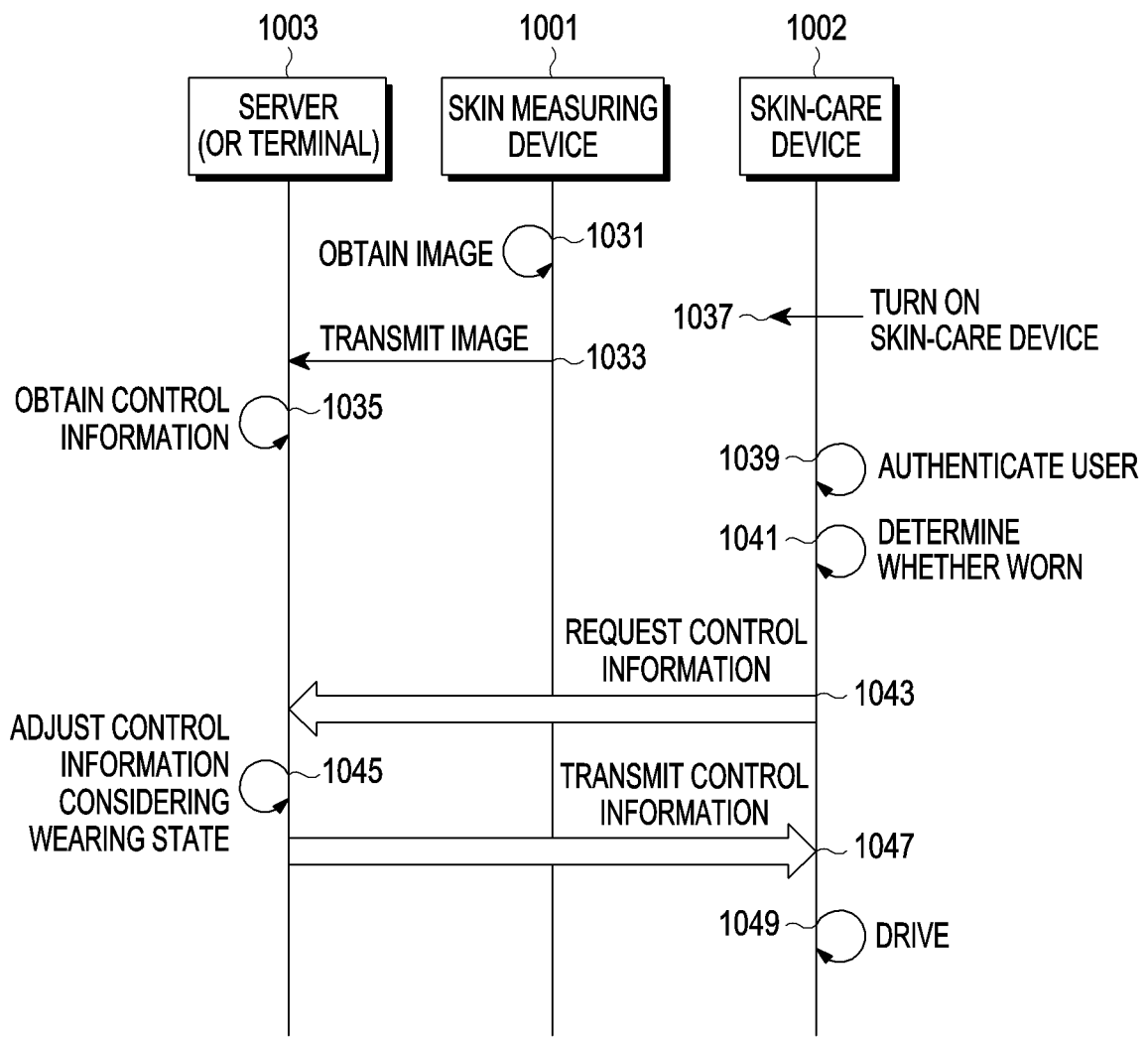

FIG. 10B is a flowchart illustrating a method in which a skin-care device 1002 obtains control information generated by a server 1003 via a skin measuring device 1001 and is driven based on the control information.

According to an embodiment, referring to FIG. 10B, the skin measuring device 1001 and the server 1003 are in a state of being unable to directly communicate with each other.

Referring to FIG. 10B, in operation 1031, the skin measuring device 1001 (e.g., the first electronic device 201 of FIG. 2B) may obtain an image including the user's face. In operation 1033, the skin measuring device 1001 may transmit the image to the server 1003 (e.g., the server 203 of FIG. 2B).

In operation 1035, the server 1003 may identify the user's skin information and face information based on the image obtained from the skin measuring device 1001. The server 1003 may generate control information corresponding to the user (or the user's face) based on the identified skin information and face information. The server 1003 may store the control information. At this time, the server 1003 may store the control information per user.

In operation 1037, the skin-care device 1002 (e.g., the second electronic device 202 of FIG. 2B) may be turned on by the user. In operation 1039, the skin-care device 1002 may request user authentication. In operation 1043, if (or based on) user authentication is successful, the skin-care device 1002 may send a request for control information to the skin measuring device 1001. The skin measuring device 1001 may send a request for control information to the server 1003 in response to (or based on) the request from the skin-care device 1002. In operation 1041, the skin-care device 1002, before requesting the control information, may identify whether the user has worn the skin-care device 1002. For example, if (or based on) the user has worn the skin-care device 1002, the skin-care device 1002 may transmit wearing information to the skin measuring device 1001 while (e.g., prior to, concurrently with, or after) requesting the control information. In contrast, if the user has not worn the skin-care device 1002, the skin-care device 1002 may request control information without transmitting the wearing information.

In operation 1045, the server 1003 may adjust the control information considering (or based on) the wearing state. For example, upon (or based on) receiving the wearing information, the server 1003 may adjust the control information based on the wearing information. Absent reception of the wearing information, the server 1003 may refrain from adjusting the control information.

In operation 1047, the server 1003 may transmit the control information to the skin measuring device 1001. The skin measuring device 1001 may transmit the received control information to the skin-care device 1002. In operation 1049, the skin-care device 1002 may be driven according to the control information.

Figure 10C:
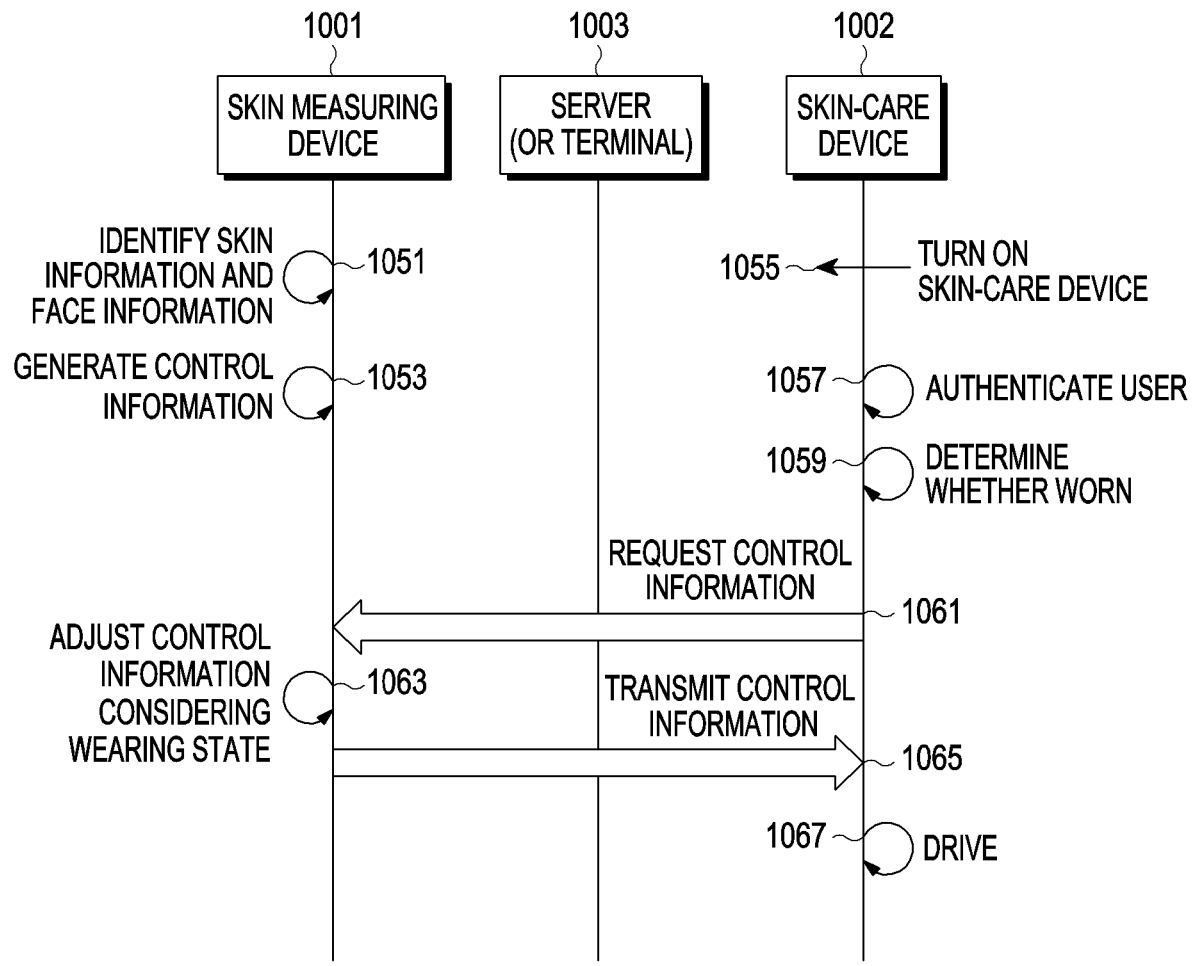

FIG. 10C is a flowchart illustrating a method in which a skin-care device 1002 obtains, via a server 1003, control information generated by a skin measuring device 1001 and is driven based on the control information.

According to an embodiment, referring to FIG. 10C, the skin measuring device 1001 and the skin-care device 1002 are in a state of being unable to directly communicate with each other. Referring to FIG. 10C, the server 1003 may be in a state of directly communicating with the skin measuring device 1001 and the skin-care device 1002.

Referring to FIG. 10C, in operation 1051, the skin measuring device 1001 (e.g., the first electronic device 201 of FIG. 2B) may identify the user's skin information and face information from an image including the user's face.

In operation 1053, the skin measuring device 1001 may generate control information corresponding to the user (or the user's face).

In operation 1055, the skin-care device 1002 (e.g., the second electronic device 202 of FIG. 2B) may be turned on by the user. In operation 1057, the skin-care device 1002 may request user authentication. In operation 1059, if user authentication is successful, the skin-care device 1002 may determine whether the user has worn the skin-care device 1002.

In operation 1061, the skin-care device 1002 may send a request for control information to the skin measuring device 1001 via the server 1003 (e.g., the server 203 of FIG. 2B). For example, if (or based on) the user has worn the skin-care device 1002, the skin-care device 1002 may transmit wearing information to the skin measuring device 1001 via the server 1003 while requesting the control information. In contrast, if (or based on) the user has not worn the skin-care device 1002, the skin-care device 1002 may request control information without transmitting the wearing information.

In operation 1063, the skin measuring device 1001 may adjust the control information considering or based on the wearing state. For example, upon (or based on) receiving the wearing information, the skin measuring device 1001 may adjust the control information based on the wearing information. Absent reception of the wearing information, the skin measuring device 1001 may refrain from adjusting the control information.

In operation 1065, the skin measuring device 1001 may transmit the control information to the skin-care device 1002 via the server 1003. In operation 1067, the skin-care device 1002 may be driven according to the control information.

As described above, the skin measuring device 1001 may transmit/receive data to/from the skin-care device 1002 via the server 1003 without direct transmission/receiving between the skin measuring device 1001 and the skin-care device 1002. In this case, in order to provide the control information to the skin-care device 1002, the skin measuring device 1001 may transmit the control information to the server 1003, and the server 1003 may then transmit the control information to the skin-care device 1002. For example, referring to FIG. 10C, the skin measuring device 1001 and the skin-care device 1002 may be in the state of being unable to directly communicate with each other.

Figure 10D:
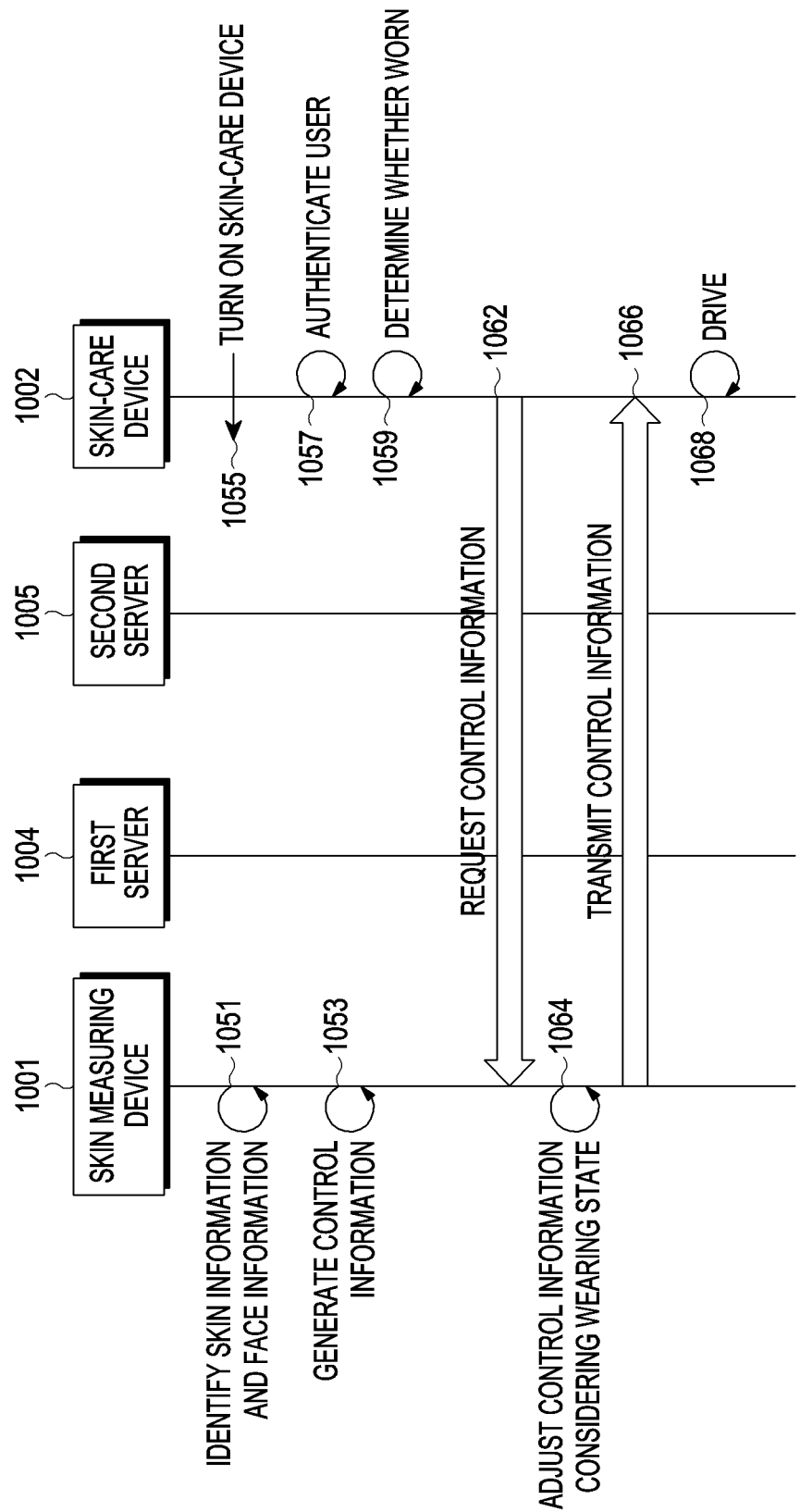

FIG. 10D is a flowchart illustrating a method in which a skin-care device 1002 obtains, via a first server 1004 and a second server 1005, control information generated by a skin measuring device 1001 and is driven based on the control information.

According to an embodiment, referring to FIG. 10D, the skin measuring device 1001 and the skin-care device 1002 are in a state of being unable to directly communicate with each other. Referring to FIG. 10D, the first server 1004 and the second server 1005 may be in a state of being able to directly communicate with each other.

Referring to FIG. 10D, according to an embodiment, the first server 1004 may be a server corresponding to the skin measuring device 1001, such as a server for managing the skin measuring device 1001. For example, the skin measuring device 1001 may transmit/receive data to/from the first server 1004.

According to an embodiment, the second server 1005 may be a server corresponding to the skin-care device 1002, such as a server for managing the skin-care device 1002. For example, the skin-care device 1002 may transmit/receive data to/from the second server 1005.

Referring to FIGS. 10C and 10D, operations 1051 to 1059 of the skin measuring device 1001 and the skin-care device 1002 as shown in FIG. 10D may be implemented identically or similarly to operations 1051 to 1059 of FIG. 10C.

In operation 1062, the skin-care device 1002 may send a request for control information to the skin measuring device 1001 via the second server 1005 and the first server 1004. For example, if (or based on) the user has worn the skin-care device 1002, the skin-care device 1002 may transmit wearing information to the skin measuring device 1001 via the second server 1005 and the first server 1004 while (e.g., prior to, concurrently with, or after) requesting the control information. In contrast, if the user has not worn the skin-care device 1002, the skin-care device 1002 may request control information without transmitting the wearing information.

In operation 1064, the skin measuring device 1001 may adjust the control information considering or based on the wearing state. For example, upon receiving the wearing information, the skin measuring device 1001 may adjust the control information based on the wearing information. Absent reception of the wearing information, the skin measuring device 1001 may refrain from adjusting the control information.

In operation 1066, the skin measuring device 1001 may transmit the control information to the skin-care device 1002 via the first server 1004 and the second server 1005. In operation 1068, the skin-care device 1002 may be driven according to the control information.

As described above, the skin measuring device 1001 may transmit/receive data to/from the skin-care device 1002 via the first server 1004 and the second server 1005 without direct communication between the skim measuring device 1001 and the skin-care device 1002. For example, in order to provide the control information to the skin-care device 1002, the skin measuring device 1001 may transmit the control information to the first server 1004. The first server 1004 may transmit the control information to the second server 1005. Thereafter, the second server 1005 may transmit the control information to the skin measuring device 1002. For example, referring to FIG. 10D, the skin measuring device 1001 and the skin-care device 1002 may be in the state of being unable to directly communicate with each other, and the skin-care device 1002 may be controlled via communication between the servers 1004 and 1005.

Figure 10E:
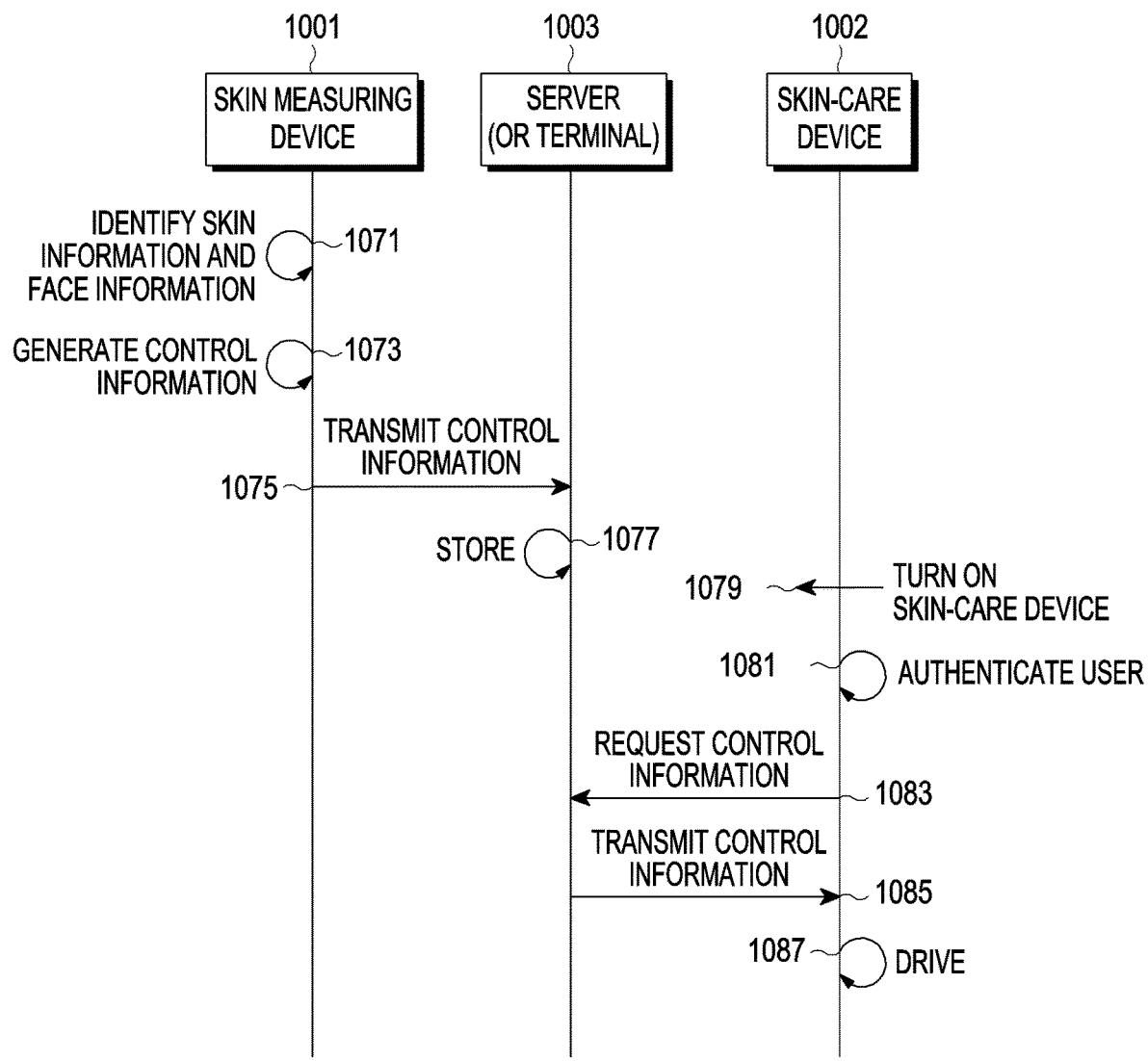

FIG. 10E is a flowchart illustrating a method in which a skin-care device 1002 obtains control information stored in a server 1003 and is driven based on the control information.

Referring to FIG. 10E, in operation 1071, the skin measuring device 1001 (e.g., the first electronic device 201 of FIG. 2B) may identify the user's skin information and face information from an image including the user's face.

In operation 1073, the skin measuring device 1001 may generate control information corresponding to the user (or the user's face). In operation 1075, the skin measuring device 1001 may transmit the control information to the server 1003 (e.g., the server 203 of FIG. 2B).

In operation 1077, the server 1003 may store the control information. For example, the server 1003 may store the control information per user.

In operation 1079, the skin-care device 1002 (e.g., the second electronic device 202 of FIG. 2B) may be turned on by the user. In operation 1081, the skin-care device 1002 may request user authentication. In operation 1083, if (or based on) user authentication is successful, the skin-care device 1002 may send a request for control information to the server 1003.

In operation 1085, the server 1003 may transmit the control information to the skin-care device 1002 in response to (or based on) the request from the skin-care device 1002. In operation 1087, the skin-care device 1002 may be driven according to the control information.

Figure 10F:
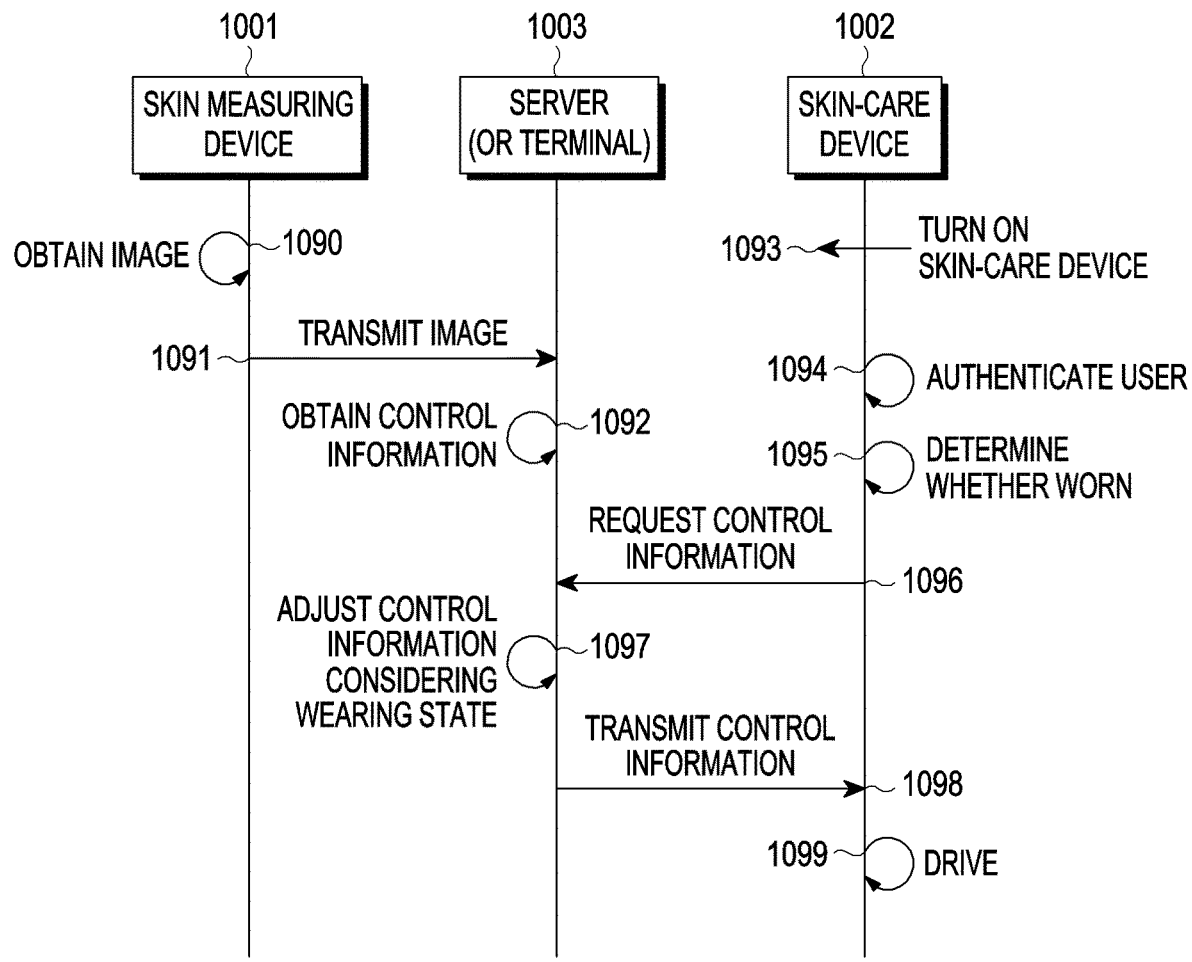

FIG. 10F is a flowchart illustrating a method in which a skin-care device 1002 obtains control information generated by a server 1003 and is driven based on the control information.

Referring to FIG. 10F, in operation 1090, the skin measuring device 1001 may obtain an image including the user's face. For example, the skin measuring device 1001 may obtain the image including the user's face using a camera (e.g., the camera 280 of FIG. 3). In operation 1091, the skin measuring device 1001 may transmit the image to the server 1003.

In operation 1092, the server 1003 may identify the user's skin information and face information based on the image obtained from the skin measuring device 1001. The server 1003 may generate control information corresponding to the user (or the user's face) based on the identified skin information and face information. The server 1003 may store the control information. For example, the server 1003 may store the control information per user.

In operation 1093, the skin-care device 1002 (e.g., the second electronic device 202 of FIG. 2B) may be turned on by the user. In operation 1094, the skin-care device 1002 may request user authentication. In operation 1096, if (or based on) user authentication is successful, the skin-care device 1002 may send a request for control information to the server 1003. In operation 1095, the skin-care device 1002, before requesting the control information, may identify whether the user has worn the skin-care device 1002. For example, if the user has worn the skin-care device 1002, the skin-care device 1002 may transmit wearing information to the server 1003 while (e.g., prior to, concurrently with, or after) requesting the control information. In contrast, if the user has not worn the skin-care device 1002, the skin-care device 1002 may request control information without transmitting the wearing information.

In operation 1097, the server 1003 may adjust the control information considering the wearing state. For example, upon (or based on) receiving the wearing information, the server 1003 may adjust the control information based on the wearing information. Absent reception of the wearing information, the server 1003 may refrain from adjusting the control information.

In operation 1098, the server 1003 may transmit the control information to the skin-care device 1002. In operation 1099, the skin-care device 1002 may be driven according to the control information.

Although FIGS. 10A to 10F illustrate four embodiments in which the skin-care device 1002 obtains control information, it is understood that one or more other embodiments are not limited thereto. For example, generation of control information by the skin measuring device 1001 and obtaining of control information by the skin-care device 1002 may be performed in different orders than those described above. For example, if the skin-care device 1002 is turned on by the user and the user authentication is successful, the skin-care device 1002 may send a request for control information to the skin measuring device 1001 or server 1003, and the skin measuring device 1001 or server 1003 may generate or obtain control information in response to (or based on) the request for control information. In other words, the skin-care device 1002 may obtain control information by various methods that may be elicited by one of ordinary skill in the art.

Figure 11A:
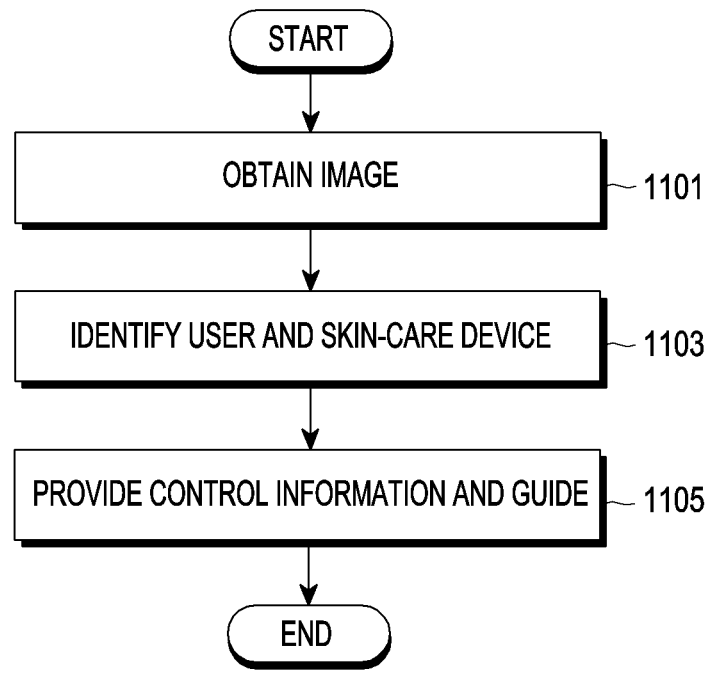
FIGS. 11A and 11B are flowcharts illustrating a method of recognizing a user and a skin-care device and providing a guide by a skin measuring device according to an embodiment.
Figure 11B:
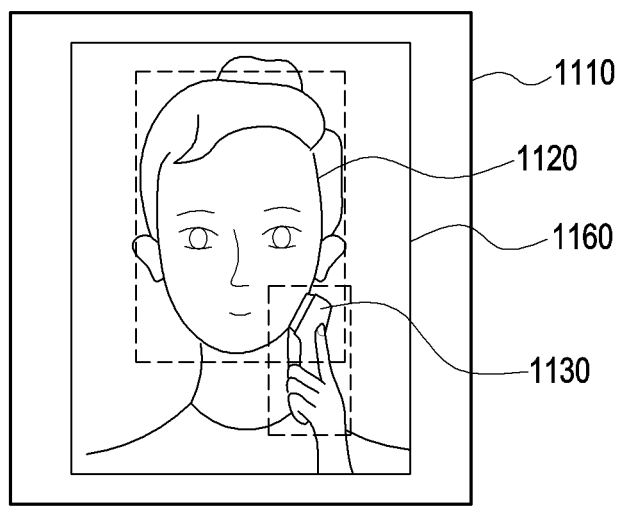

FIGS. 11A and 11B are flowcharts illustrating a method of recognizing a user and a skin-care device and providing a guide by a skin measuring device according to an embodiment.

Referring to FIGS. 11A and 11B, in operation 1101, a skin measuring device 1110 may obtain an image from a camera included in the skin measuring device 1001. At this time, the image may include the user's face and a skin-care device 1130. For example, the skin measuring device 1110 may be positioned near the skin-care device 1130.

Referring to FIG. 11B, the skin measuring device 1110 may be implemented as a smart mirror. For example, if the user holds the skin-care device 1130 in front of the smart mirror, the skin measuring device 1110 may obtain an image including the user's face 1120 and the skin-care device 1130.

In operation 1103, the skin measuring device 1110 may recognize the user (or the user's face) 1120 and the skin-care device 1130 from the image. The skin measuring device 1110 may recognize at least one of the user's gesture or motion based on the recognized user (or user's face) 1120 and the skin-care device 1130. The skin measuring device 1110 may obtain control information based on the recognized at least one of user face 1120, skin-care device 1130, and user motion. For example, the skin measuring device 1110 may newly generate control information from the image or read pre-stored control information.

Referring to FIG. 11B, if the user holds the skin-care device 1130 in front of the camera of the smart mirror, the smart mirror 1110 may recognize the user's face 1120 and the skin-care device 1130. The smart mirror 1110 may identify the kind of the skin-care device 1130 and recognize the user's motion. For example, if the skin-care device 1130 is a galvanic massager, the smart mirror 1110 may recognize that the user will use the galvanic massager 1130. The smart mirror 1110 may obtain adequate control information when the user uses the galvanic massager 1130.

In operation 1105, the skin measuring device 1110 may provide the obtained control information to the skin-care device 1130. The skin measuring device 1110 may provide the user with guide information that helps using the skin-care device 1130.

Referring to FIG. 11B, the smart mirror 1110 may provide the control information to the galvanic massager 1130. The smart mirror 1110 may display the guide information, which helps using the galvanic massager 1130, on the display 1160.

Figure 12:
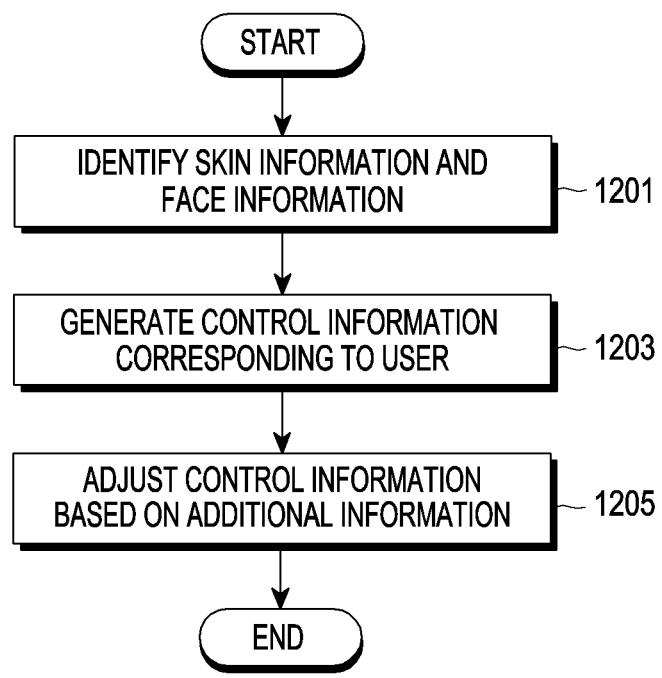
FIG. 12 is a flowchart illustrating a method of generating a control program for controlling a skin-care device based on additional information by a skin measuring device according to an embodiment.

FIG. 12 is a flowchart illustrating a method of generating a control program for controlling a skin-care device based on additional information by a skin measuring device according to an embodiment.

Referring to FIG. 12, in operation 1201, the skin measuring device (e.g., the first electronic device 201 of FIG. 2) may identify the user's skin information and face information from an image including the user's face.

In operation 1203, the skin measuring device 201 may generate control information corresponding to the user.

In operation 1205, the skin measuring device 201 may adjust the control information based on additional information. For example, the additional information may include information about the ambient environment including at least one of weather, season, fine dust level, ultraviolet (UV) level, external temperature, external humidity, and/or place of residence that is obtained from an external electronic device (or an external server). The additional information may also include the user's habit (such as habits for smoking, sleeping, drinking, and eating), place of residence, age, gender, race, and/or genetic information entered by the user.

According to an embodiment, if a fine dust concentration is high and the user is exposed to fine dust for a long time, the skin measuring device 201 may generate control information to control the LED mask (e.g., the second electronic device 202 of FIG. 2) to emit blue light so as to perform care for antibacterial effects and skin soothing.

According to an embodiment, if the user is a smoker, the skin measuring device 201 may generate control information to control the LED mask 202 to radiate red light so as to perform care to increase skin elasticity and reduce wrinkles.

Figure 13:
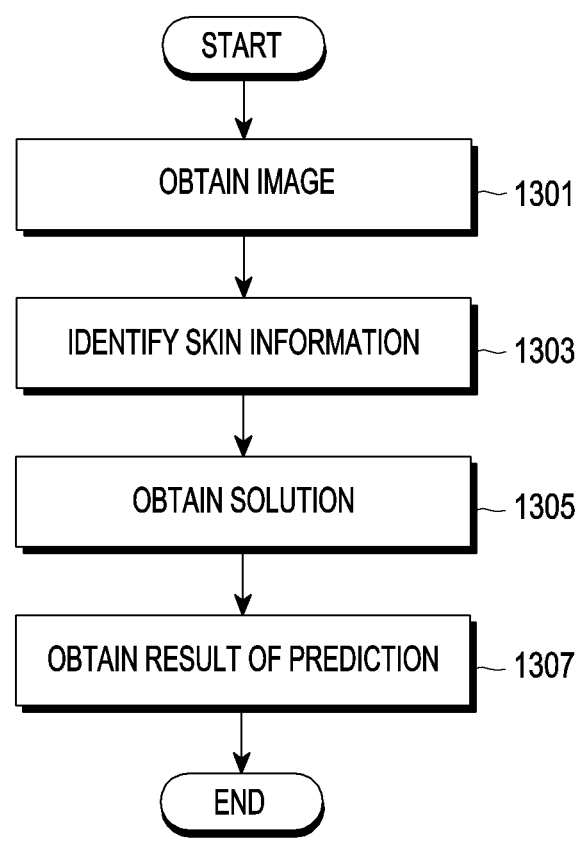
FIG. 13 is a flowchart illustrating a method of providing a solution for a skin-care device by a server according to an embodiment.

FIG. 13 is a flowchart illustrating a method of providing a solution for a skin-care device by a server according to an embodiment.

Referring to FIG. 13, in operation 1301, a server (e.g., the server 203 of FIG. 2B) may obtain an image including the user's face from a skin measuring device (e.g., the first electronic device 201 of FIG. 2B).

In operation 1303, the server 203 may identify (or determine) the user's skin information (e.g., the user's skin condition and skin feature). For example, the server 203 may identify the user's skin information based on artificial intelligence that includes element techniques, such as machine learning (deep learning) that utilizes algorithms capable of classifying and learning the features of entered data on their own and copying the perception or determination by the human brain using machine learning algorithms.

In operation 1305, the server 203 may analyze the user's skin information (e.g., the user's skin condition and skin feature), thereby obtaining (or deriving) a solution (or solution information). For example, the solution may be or include a method for enhancing the user's current skin (e.g., skin condition). The solution may be determined considering the user's current skin condition and skin features. The solution may include a method of using at least one skin-care device. For example, the server 203 may obtain the solution based on artificial intelligence that includes element techniques, such as machine learning (deep learning) that utilizes algorithms capable of classifying and learning the features of entered data on their own and copying the perception or determination by the human brain using machine learning algorithms.

In operation 1307, the server 203 may obtain information about a result predicted or expected when the user normally performs the solution. For example, the server 203 may obtain the information about the predicted result based on artificial intelligence that includes element techniques, such as machine learning (deep learning) that utilizes algorithms capable of classifying and learning the features of entered data on their own and copying the perception or determination by the human brain using machine learning algorithms.

According to an embodiment, the server 203 may represent the skin condition expected when the user applies the solution in the form of variations over time and provide the same to the user (or the user's terminal).

Figure 14:
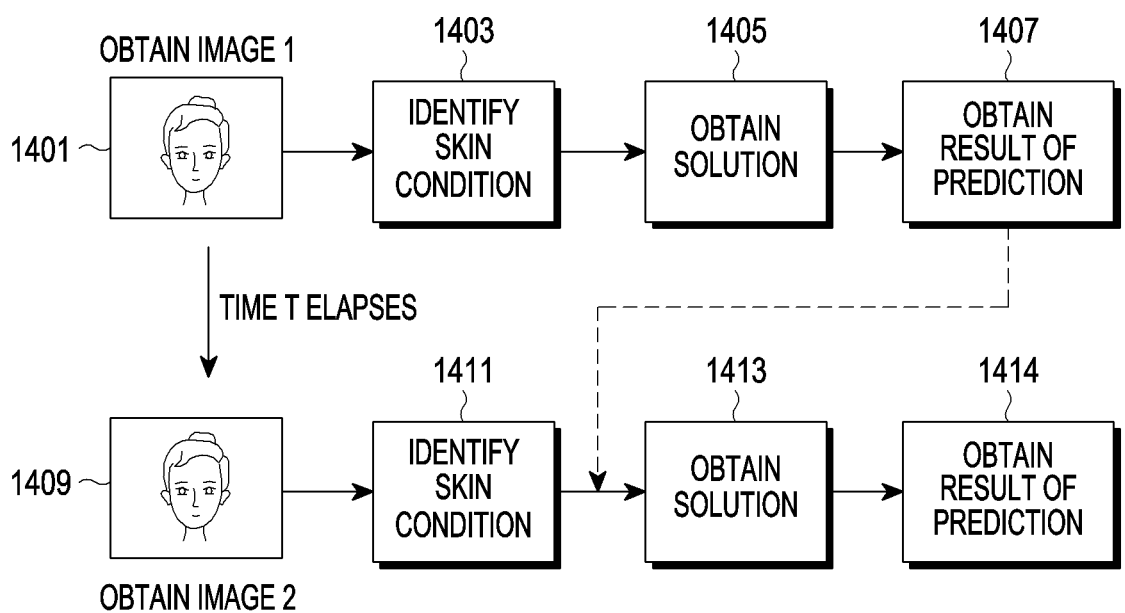
FIG. 14 is a view illustrating a method of providing a solution for a skin-care device by a server according to an embodiment.

FIG. 14 is a view illustrating a method of providing a solution for a skin-care device by a server according to an embodiment.

Referring to FIG. 14, according to an embodiment, a server (e.g., the server 203 of FIG. 2B) may elicit (or obtain or determine) the resultant values based on artificial intelligence that includes element techniques, such as machine learning (deep learning) that utilizes algorithms capable of classifying and learning the features of entered data on their own and copying the perception or determination by the human brain using machine learning algorithms.

In operation 1401, the server 203 may obtain a first image including the user's face from a skin measuring device (e.g., the first electronic device 201 of FIG. 2B).

In operation 1403, the server 203 may identify the user's skin condition from the first image. The server 203 may also identify the user's skin feature from the first image.

In operation 1405, the server 203 may obtain (or derive, determine, etc.) a solution for enhancing the user's skin condition based on the user's current skin condition (and skin feature). For example, the server 203 may provide (or transmit) the solution to the skin-care device (e.g., the second electronic device 202 of FIG. 2B) and/or the user's terminal. For example, the solution may be solution A.

In operation 1407, the server 203 may obtain (or derive, determine, etc.) the results for skin condition predicted when the user performs skin care according to the solution.

In operation 1409, after a specific time (time t) elapses, the server 203 may obtain a second image including the user's face from the skin measuring device (e.g., the first electronic device 201 of FIG. 2B).

In operation 1411, the server 203 may identify the user's skin condition from the second image.

In operation 1413, the server 203 may obtain (or derive, determine, etc.) a solution for enhancing the user's skin condition based on the user's current skin condition and the predicted result of the solution obtained (or derived, determined, etc.) before the specific time (time t) (e.g., the predicted result is or includes the result for the skin condition predicted or expected when (or based on) the user performs skin care according to the solution and is hereinafter referred to as a "prediction result of solution"). For example, the solution may be solution A that is identical to a prior solution, or may be solution B that is a new, different solution from solution A given the current skin condition and the prediction result of the solution previously provided. The server 203 may obtain the solution further considering the degree to which the user has performed the previously-provided solution.

As set forth above, if considering the prediction result of the previously-provided solution (e.g., solution A), although the same (or similar) skin condition is measured on the same user after the time elapses, the server 203 may obtain (or derive, determine, etc.) another solution that is more appropriate for the user. For example, in a case where the server 203 provides a solution according to the user's skin condition based on artificial intelligence without considering the prediction result of the previously-provided solution, if the same (or similar) skin condition is measured on the same user, the server 203 may obtain and provide only the same solution all the time. For example, the server 203 may make a change to the solution by applying the degree of enhancement (e.g., worse, better, no change, a reference level or less enhanced, or drastically enhanced) as compared with the current skin condition and the prediction result of the previously provided solution. In other words, according to an embodiment, if the prediction result of the solution previously provided is taken into consideration, although the same (or similar) skin condition is measured on the same user, the server 203 may provide the same solution as the prior solution (e.g., solution A) or a new different solution (e.g., solution B) from the prior solution. Thus, according to an embodiment, the server 203 may obtain and provide the optimal solution for enhancing the user's skin condition considering the degree of fitness between the user's skin condition and the solution. For example, the degree of fitness between the user's skin condition and solution may be determined depending on the degree of skin enhancement (e.g., the degree of drastic enhancement over time) when the user applies the solution and, if the degree of fitness increases, the solution may exhibit a larger enhancement to the user.

In operation 1414, the server 203 may obtain (or derive, determine, etc.) the results for skin condition predicted when the user performs skin care according to the solution. For example, the prediction result obtained in operation 1414 may be considered in obtaining the solution after the specific time elapses (e.g., the specific time after the second image is obtained). For example, the server 203 may obtain and provide the solution for enhancing the user's skin condition again after a specific time has elapsed from when the second image is obtained. At this time, the server 203 may consider the prediction result elicited upon obtaining the second image in obtaining the solution. As described above, the server 203 may consider the prediction result of the previously-provided solution in deriving the solution.

According to an embodiment, the server 203 may obtain and provide information indicating the degree of enhancement in the user's skin condition after the specific time elapses. The server 203 may generate control information based on the newly-provided solution and provide (or transmit) the generated control information to the skin-care device 202.

Figure 15:
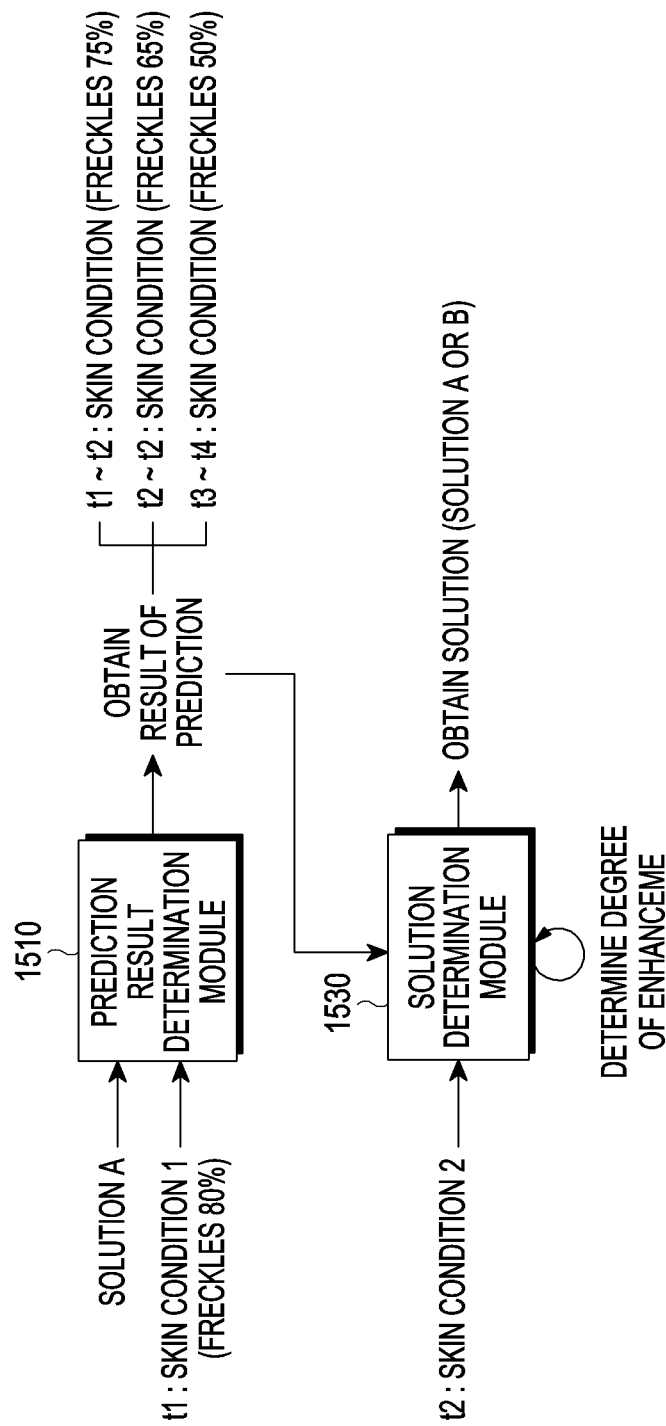
FIG. 15 is a view illustrating a method of providing a solution for a skin-care device by a server according to an embodiment.

FIG. 15 is a view illustrating a method of providing a solution for a skin-care device by a server according to an embodiment.

Referring to FIG. 15, a server (e.g., the server 203 of FIG. 2B) may include a prediction result determination module 1510 (e.g., prediction result determiner) and a solution determination module 1530 (e.g., solution determiner).

According to an embodiment, the prediction result determination module 1510 may be a module that determines a result (e.g., a predicted skin condition) predicted when the user applies a specific solution and obtains (or derives, determines, etc.) the determined prediction result. For example, the operation of the prediction result determination module 1510 may correspond to operation 1407 of FIG. 14.

According to an embodiment, the solution determination module 1530 may be a module that determines a solution for the user's skin care and obtains and provides the determined solution. For example, the operation of the solution determination module 1530 may correspond to operation 1413 of FIG. 15.

According to an embodiment, the prediction result determination module 1510 may obtain per-time prediction results based on a previously-provided solution (e.g., solution A provided at time t1) and the user's skin condition at a specific time (e.g., time t1). For example, the prediction result may be or include information indicating the degree of enhancement in the user's skin condition that is expected when the solution previously provided to the user applies. For example, if the user's skin condition is "freckles 80%" at time t1, and solution A is provided, the prediction result determination module 1510 may predict a skin condition of "freckles 75%" from t1 to t2, a skin condition of "freckles 65%" from t2 to t3, and a skin condition of "freckles 50%" from t3 to t4.

According to an embodiment, the solution determination module 1530 may determine how adequate the previously-provided solution is for the user based on the prediction results of the previously-provided solution (e.g., solution A) and the user's skin condition at a specific time (e.g., time t2 which is after time t elapses from time t1). In other words, the solution determination module 1530 may determine the degree of fitness between the user's skin condition and the previously-provided solution. For example, the solution determination module 1530 may compare the prediction result and the user's skin condition at time t2, thereby determining whether the degree of enhancement in the skin condition from t1 to t2 is large or small. The solution determination module 1530 may determine how adequate the solution is for the user based on the degree of enhancement. For example, if the skin condition is "freckles 70% to 75%" at time t2, the solution determination module 1530 may determine that the solution is appropriate for the user. In contrast, if the skin condition is "freckles 78%" at time t2, the solution determination module 1530 may determine that the solution is inappropriate for the user. In other words, the solution determination module 1530 may use the prediction result determined at a prior time so as to determine the degree of fitness between the previously-provided solution and the user's skin condition (the user's skin).

According to an embodiment, the solution determination module 1530 may determine how adequate the previously provided solution is for the user based on at least one of the prediction results of the previously provided solution (e.g., solution A provided at time t1), the content of the previously provided solution, and the user's skin condition at a specific time (e.g., time t2).

According to an embodiment, to determine the degree (or degree of fitness) to which the previously provided solution is appropriate for the user or the user's skin, the solution determination module 1530 may make use of values indicating the degree of enhancement according to each preset time (e.g., a common degree of enhancement by a specific solution) or a graph with the values. In other words, the solution determination module 1530 may compare an actual degree of enhancement in the user with value variation data indicating a pre-defined degree of enhancement over time corresponding to a difference between t2 and t1 (e.g., the degree of enhancement expected when the solution applies based on clinical data), thereby determining whether degree of enhancement in the skin condition is large or small.

According to an embodiment, the solution determination module 1530 may analyze the degree of fitness between the user and the solution provided at time t1 and, according to a result of analysis, obtain (or derive, determine, etc.) a new solution (e.g., solution B) at time t2, or the same solution (e.g., solution A) as that provided at time t1.

Figures 16A, 16B:
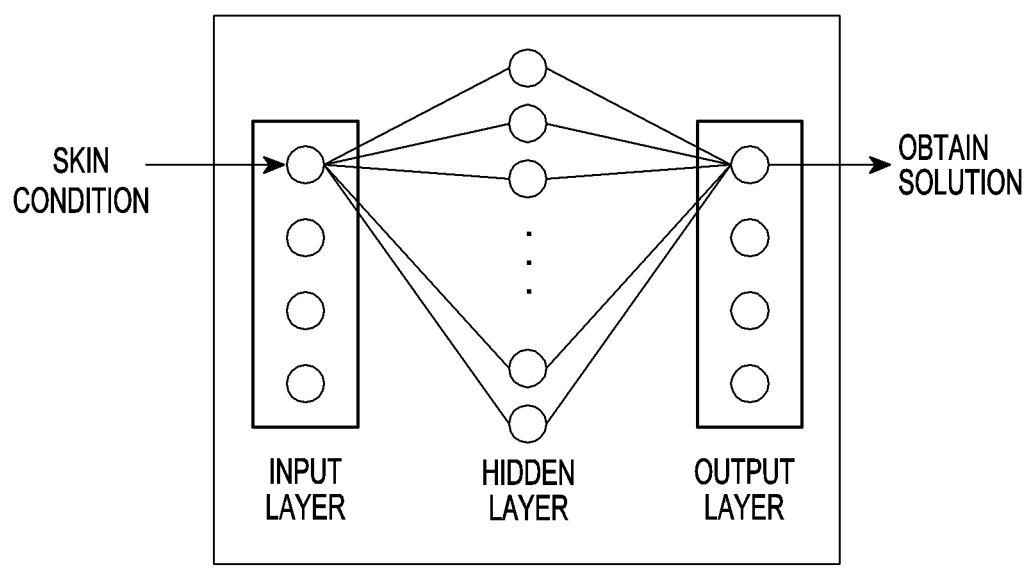
FIGS. 16A and 16B are views illustrating a method of providing a solution for a skin-care device by a server according to an embodiment.

FIGS. 16A and 16B are views illustrating a method of providing a solution for a skin-care device by a server according to an embodiment.

Referring to FIG. 16A, a server (e.g., the server 203 of FIG. 2B) may determine weights corresponding to the degrees of fitness of solutions for the user. For example, the degree of fitness between the user's skin condition and solution may be determined depending on (or based on) the degree of skin enhancement (e.g., the degree of drastic enhancement over time) when the user applies the solution and, if (or based on) the degree of fitness increases, the solution may exhibit a larger enhancement to the user. The server 203 may determine weights indicating the degrees of fitness of the solutions with reference to a total sum of 1. For example, at time t1, the server 203 may determine 0.5 for solution 1, 0.2 for solution 2, and 0.3 for solution 3. At time t2 which is after time t elapses from time t1, the server 203 may update the weight based on the degree of fitness between the user (or user's skin) and the solution. For example, when applying solution 1 from t1 to t2, the server 203 may update the weight depending on (or based on) the degree of enhancement in the user's skin condition. For example, at time t2, the server 203 may determine 0.6 for solution 1, 0.15 for solution 2, and 0.25 for solution 3. In other words, upon determining that the user's skin has been enhanced the prediction result or better by solution 1, the server 203 may increase the weight for solution 1 while reducing the weights for the other solutions.

Referring to FIG. 16B, the server 203 may modify the weight for the output layer among the plurality of layers (e.g., input layer, hidden layer, and output layer) of a solution deriving model based on the degrees of fitness of the user per solution. The server 203 may obtain a solution based on the modified weight. For example, the server 203 may obtain a solution by modifying the weight of the output layer at the stage corresponding to the SoftMax in the artificial neural network circuit.

Figure 17:
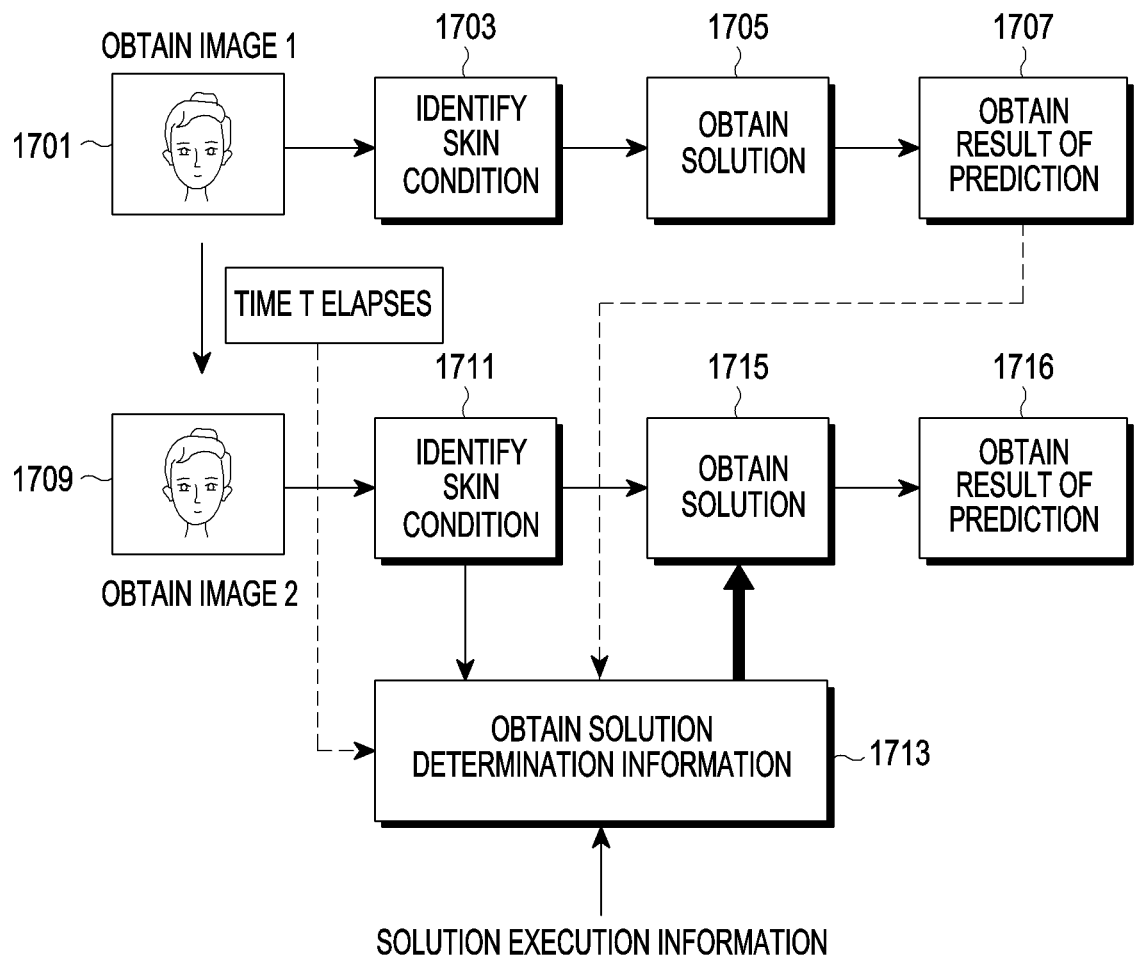
FIG. 17 is a view illustrating a method of providing a solution for a skin-care device by a server according to an embodiment.

FIG. 17 is a view illustrating a method of providing a solution for a skin-care device by a server according to an embodiment.

Referring to FIG. 17, according to an embodiment, a server (e.g., the server 203 of FIG. 2B) may obtain (or elicit, determine, etc.) the resultant values based on artificial intelligence that includes element techniques, such as machine learning (deep learning) that utilizes algorithms capable of classifying and learning the features of entered data on their own and copying the perception or determination by the human brain using machine learning algorithms.

In operation 1701, the server 203 may obtain a first image including the user's face from a skin measuring device (e.g., the first electronic device 201 of FIG. 2B). For example, the first image may be or include an image captured at a specific time t1. The first image may indicate the user's skin condition at time t1.

In operation 1703, the server 203 may identify the user's skin condition from the first image. The server 203 may also identify the user's skin feature from the first image.

In operation 1705, the server 203 may obtain (or provide, determine, etc.) a solution for enhancing the user's skin condition based on the user's current skin condition (and skin feature). For example, the server 203 may provide the solution to the skin-care device (e.g., the second electronic device 202 of FIG. 2B) and/or the user's terminal. For example, the solution may be solution A.

In operation 1707, the server 203 may obtain (or derive, determine, etc.) the results for skin condition predicted when the user performs skin care according to the solution.

In operation 1709, after a specific time (time t) elapses, the server 203 may obtain a second image including the user's face from the skin measuring device 201. For example, the second image may be an image captured at a specific time t2. The second image may indicate the user's skin condition at time t2.

In operation 1711, the server 203 may identify the user's skin condition from the second image.

In operation 1713, the server 203 may obtain information for determining a solution. For example, the server 203 may identify how much time after time t1 has elapsed to time t2. The server 203 may identify the result for the skin condition predicted at time t2. For example, the server 203 may compare the skin condition predicted when the user applied solution A at time t1 with the current skin condition (at time t2). The server 203 may further consider the degree to which the user has performed the previously provided solution. For example, the server 203 may identify, from the user, history information as to whether and/or how many times the user has performed the solution from time t1 to time t2. Further, the server 203 may consider information for the content of the solution provided to the user at time t1.

In operation 1715, the server 203 may obtain (and provide) a solution for enhancing the user's skin condition based on at least one of the pieces of information obtained in operation 1713. For example, the solution may be solution A which is identical to a prior solution (e.g., the solution at time t1) or may be solution B which is a new or different solution from solution A given (or based on) the current skin condition and the prediction result of the solution previously provided. Further, the server 203 may obtain (or provide, determine, etc.) a solution based on history information as to whether and/or how many times the user has performed the solution from time t1 to time t2 from the user. For example, if the server 203 proposed a solution of using the LED mask three times for a month, but the user didn't perform the solution, the server 203 may obtain (and provide) a solution that allows the LED mask to emit more light or in which the number of times has been varied.

In operation 1716, the server 203 may obtain (or derive, determine, etc.) the results for skin condition predicted when the user performs skin care according to the solution. For example, the prediction result derived in operation 1715 may be considered in determining the solution obtained (or derived) a specific time after time t2 elapses.

According to an embodiment, the server 203 may provide information indicating the degree of enhancement in the user's skin condition at time t2. The server 203 may generate control information based on the solution and provide the generated control information to the skin-care device 202.

According to an embodiment, an electronic device includes a camera and at least one processor configured to identify skin information indicating a user's skin condition from an image including the user's face obtained via the camera, generate control information for controlling a skin-care device to perform skin care appropriate for the user based on the skin information and information indicating the shape and function of the skin-care device, and transmit the control information to the skin-care device.

The processor may be configured to identify the skin condition for each of a plurality of regions included in the user's face using the skin information, identify the shape of the face based on the size of the user's face, face curves, and positions of features, and identify at least one position that requires (or is suitable or determined for) skin care in the user's face based on the skin condition for each of the plurality of regions and the face shape.

The processor may be configured to obtain coordinate information for coordinates into which a position of each of the plurality of regions in the user's face has been converted and identify at least one position that requires (or is suitable or determined for) skin care in the user's face based on the skin information and a shape of the skin-care device.

The processor may be configured to generate the control information based on a kind (or type) and position of a skin trouble included in the user's face.

The control information may include information for controlling at least one of a wavelength, a strength, or an output time of light output from each of a plurality of light output elements included in the skin-care device.

The control information may include information for controlling at least one of a current level or a driving time for driving the skin-care device.

The processor may be configured to adjust the control information based on information for an ambient environment including at least one of weather, season, or place of residence obtained from an external electronic device.

The processor may be configured to adjust the control information based on additional information including at least one of the user's habit, age, gender, race, genetic information, etc.

The processor may be configured to adjust the control information based on wearing information obtained from the skin-care device when (or based on) the user wears the skin-care device.

The processor may be configured to display guide information related to the control information via a display of the electronic device when the user and the skin-care device are recognized via the camera.

The skin-care device may include a mask-type skin-care device or a handheld-type skin-care device.

According to an embodiment, a method of operating an electronic device includes identifying skin information indicating a user's skin condition from an image including the user's face obtained via a camera of the electronic device, generating control information for controlling a skin-care device to perform skin care appropriate (or determined) for the user based on the skin information and information indicating the shape and function of the skin-care device, and transmitting the control information to the skin-care device.

Generating the control information may include identifying the skin condition for each of a plurality of regions included in the user's face using the skin information, identifying the shape of the face based on at least one of the size of the user's face, face curves, and positions of features, and identifying at least one position that requires (or is suitable or determined for) skin care in the user's face based on the skin condition for each of the plurality of regions and the face shape.

Generating the control information may include obtaining coordinate information for coordinates into which a position of each of the plurality of regions in the user's face has been converted and identifying at least one position that requires (or is suitable or determined for) skin care in the user's face based on the skin information and a shape of the skin-care device.

Generating the control information may include adjusting the control information based on wearing information obtained from the skin-care device when (or based on) the user wears the skin-care device.

According to an embodiment, an electronic device includes a communication module and at least one processor configured to identify whether a user is a user registered in the electronic device by comparing authentication information received from the user or a user terminal with pre-registered user information, if (or based on) the user is the registered user, send a request for control information for performing skin care appropriate (or determined) for the user to an external electronic device via the communication module, and drive the electronic device based on the control information obtained from the external electronic device via the communication module, wherein the control information may be generated based on information indicating a shape and function of the electronic device and skin information indicating the user's skin condition from an image indicating the user's face by the external electronic device.

According to an embodiment, an electronic device includes a communication module and at least one processor configured to identify skin information indicating a user's skin condition from an image including the user's face obtained via the communication module from an external electronic device, generate control information for controlling a skin-care device to perform skin care appropriate (or determined) for the user based on the skin information and information indicating the shape and function of the skin-care device, and transmit the control information to the skin-care device.

Each of the aforementioned components of the electronic device may include one or more parts, and a name of the part may vary with a type of the electronic device. The electronic device in accordance with various embodiments of the disclosure may include at least one of the aforementioned components, omit some of the aforementioned components, or include other additional component(s). Some of the components may be combined into an entity, but the entity may perform the same functions as the components may do.

As is apparent from the foregoing description, according to various embodiments of the disclosure, the electronic device may control the skin-care device to perform care appropriate for the user's skin condition and face shape, thereby providing user-customized skin care.

The embodiments disclosed herein are provided for description and understanding of the disclosed inventive concept(s) and does not limit the scope of the disclosure. Accordingly, the scope of the disclosure should be interpreted as including all changes or various embodiments based on the technical spirit of the disclosure.

What is claimed is:

1. An electronic device, comprising:
   a camera; and
   at least one processor configured to:
      determine, from an image including a face of a user obtained via the camera, skin information indicating a skin condition of the user,
      generate control information for controlling a skin-care device to perform care based on the determined skin information and information regarding the skin-care device, and
      transmit the control information to the skin-care device,
   wherein the at least one processor is configured to:
      based on receiving, from the skin-care device, wearing information including a degree of tightness between the user's face skin and the skin-care device when the user wears the skin care-device, adjust the control information based on the wearing information.

2. The electronic device of claim 1, wherein the at least one processor is further configured to:
   determine a skin condition for each of a plurality of regions included in the face of the user;
   determine a shape of the face based on at least one of a size of the face, a curve of the face, and a size and a position of a feature of the face; and
   determine at least one position for skin care in the face based on the skin condition for each of the plurality of regions and the shape of the face.

3. The electronic device of claim 2, wherein the at least one processor is further configured to:
   obtain coordinate information for coordinates corresponding to a position of each of the plurality of regions; and
   determine at least one position for the skin care in the face based on the skin information and a shape of the skin-care device.

4. The electronic device of claim 1, wherein the at least one processor is further configured to generate the control information based on a kind and a position of a skin trouble included in the face of the user.

5. The electronic device of claim 1, wherein the control information comprises information for controlling at least one of a wavelength, a strength, and an output time of light output from each of a plurality of light output elements included in the skin-care device.

6. The electronic device of claim 1, wherein the control information comprises information for controlling at least one of a current level and a driving time for driving the skin-care device.

7. The electronic device of claim 1, wherein the at least one processor is further configured to adjust the control information based on information on an ambient environment including at least one of weather, season, and place of residence obtained from an external electronic device.

8. The electronic device of claim 1, wherein the at least one processor is further configured to adjust the control information based on additional information including at least one of a habit, an age, a gender, a race, and genetic information of the user.

9. The electronic device of claim 1, wherein the at least one processor is further configured to:

receive, from the skin-care device, the wearing information indicating a wearing state of the skin-care device, the wearing state including the degree of tightness between the user's face skin and the skin-care device.

10. The electronic device of claim 1, wherein the at least one processor is further configured to, based on recognizing at least one of the user and the skin-care device via the camera, obtain the control information corresponding to the at least one of the user and the skin-care device and provide the control information to the skin-care device.

11. The electronic device of claim 1, wherein the at least one processor is further configured to display guide information related to the control information via a display of the electronic device.

12. A method for operating an electronic device, the method comprising:
 determining, from an image including a face of a user obtained via a camera of the electronic device, skin information indicating a skin condition of the user;
 generating control information for controlling a skin-care device to perform care based on the determined skin information and information regarding the skin-care device;
 transmitting the control information to the skin-care device,
 wherein the method further comprises:
 based on receiving, from the skin-care device, wearing information including a degree of tightness between the user's face skin and the skin-care device when the user wears the skin care-device, adjusting the control information based on the wearing information.

13. The method of claim 12, wherein the generating the control information comprises:
 determining a skin condition for each of a plurality of regions included in the face;
 determining a shape of the face based on at least one of a size of the face, a curve of the face, and a size and a position of a feature of the face; and
 determining at least one position for skin care in the face based on the skin condition for each of the plurality of regions and the shape of the face.

14. The method of claim 13, wherein the generating the control information further comprises:
 obtaining coordinate information for coordinates corresponding to a position of each of the plurality of regions; and
 determining at least one position for the skin care in the face based on the skin information and a shape of the skin-care device.

15. The method of claim 12, wherein the generating the control information comprises:
 receiving, from the skin-care device, the wearing information indicating a wearing state of the skin-care device, the wearing state including the degree of tightness between the user's face skin and the skin-care device.

16. An electronic device, comprising:
 a communicator; and
 at least one processor configured to:
 determine whether a user is registered in the electronic device by comparing authentication information received from the user or a user terminal with pre-registered user information,
 based on the user being determined to be registered, send a request for control information for performing skin care appropriate for the user to an external electronic device via the communicator, and
 drive the electronic device based on the control information obtained from the external electronic device via the communicator,
 wherein the control information is generated by the external electronic device based on information indicating a shape and a function of the electronic device, skin information indicating a skin condition of the user determined from an image including a face of the user, and a wearing state including a degree of tightness between the user's face skin and the electronic device when the user wears the electronic device.

17. The electronic device of claim 16, wherein:
 the at least one processor is further configured to determine the wearing state of the electronic device via at least one proximity sensor included in the electronic device and to transmit information on the wearing state to the external electronic device; and
 the control information is generated based on the information on the wearing state.

18. The electronic device of claim 16, further comprising:
 a plurality of optical elements,
 wherein the at least one processor is further configured to control at least one of a wavelength, a strength, and an output time of light output from each of the plurality of optical elements based on the control information.

19. The electronic device of claim 16, wherein the at least one processor is further configured to control at least one of a vibration strength, a vibration period, and a driving time of a vibrating device included in the electronic device based on the control information.

20. The electronic device of claim 16, wherein the at least one processor is further configured to obtain, from the external electronic device, guide information indicating a method of caring for skin of the user using the electronic device and to provide the obtained guide information to the user.

* * * * *